(12) United States Patent
Kwiatkowski et al.

(10) Patent No.: US 8,263,752 B2
(45) Date of Patent: Sep. 11, 2012

(54) METHODS FOR SEPARATING SOLUBLE SELENOGLYCOPROTEINS

(75) Inventors: Stefan Kwiatkowski, Lexington, KY (US); Ronan Power, Lexington, KY (US); Clayton Matney, Nicholasville, KY (US); Paiman P. Ghoroghchian, Downingtown, PA (US); Eric M. Ostertag, Lexington, KY (US)

(73) Assignee: Alltech, Inc., Nicholasville, KY (US)

( * ) Notice: Subject to any disclaimer, the term of this patent is extended or adjusted under 35 U.S.C. 154(b) by 0 days.

(21) Appl. No.: 13/051,646

(22) Filed: Mar. 18, 2011

(65) Prior Publication Data

US 2011/0280948 A1 Nov. 17, 2011

Related U.S. Application Data

(60) Provisional application No. 61/315,265, filed on Mar. 18, 2010.

(51) Int. Cl.
*C07K 1/30* (2006.01)
*C07K 1/36* (2006.01)

(52) U.S. Cl. ......... 530/418; 530/412; 530/419; 530/395

(58) Field of Classification Search .................. None
See application file for complete search history.

(56) References Cited

U.S. PATENT DOCUMENTS

| | | | |
|---|---|---|---|
| 5,221,545 | A | 6/1993 | Borschel |
| 5,959,050 | A | 9/1999 | Mosbach |
| 6,197,295 | B1 | 3/2001 | Hsia |
| 6,576,233 | B2 | 6/2003 | Hsia |
| 6,835,394 | B1 | 12/2004 | Discher |
| 6,911,550 | B2 | 6/2005 | Abdel-Monem |
| 7,498,045 | B2 | 3/2009 | Chang |
| 7,682,603 | B2 | 3/2010 | Hammer |
| 7,867,512 | B2 | 1/2011 | Discher |
| 2001/0043925 | A1 | 11/2001 | Hsia |
| 2004/0254239 | A1 | 12/2004 | Abdel-Monem |
| 2005/0019265 | A1 | 1/2005 | Hammer |
| 2005/0069594 | A1 | 3/2005 | Lubinski |
| 2005/0089530 | A1 | 4/2005 | Moesgaard |
| 2005/0123617 | A1 | 6/2005 | Chang |
| 2006/0263415 | A1 | 11/2006 | Sedmak |
| 2007/0218123 | A1 | 9/2007 | Discher |
| 2008/0107755 | A1 | 5/2008 | Lyons |

OTHER PUBLICATIONS

Takahashi et al., "Purification and characterization of human plasma glutathione peroxidase: a selenoglycoprotein distinct from the known cellular enzyme.", Archives of Biochemistry and Biophysics, Aug. 1987, 256(2):677-686.*
Andersson, et al., Molecular Interactions in Bioseparations (Ngo. T. T. ed.), pp. 383-394 (book), 1993.
Bedwal, R. S. et al., "Selenium—its biological perspectives", Medical Hypotheses vol. 41, No. 2, Aug. 1993, pp. 150-159.
Brooks et al., "Plasma selenium level before diagnosis and the risk of prostate cancer development." J Urol vol. 166, 2001, pp. 2034-2038.
Clark et al., "Effects of selenium supplementation for cancer prevention in patients with carcinoma of the skin. A randomized controlled trial. Nutritional Prevention of Cancer Study Group" J Am Med Assoc vol. 276, 1996, pp. 1957-1963.
Combs, G.F.; Grey, W.P. 'Chemopreventive Agents: Selenium' Pharmacol. Ther. 79, 179-192 (1998).
Couvreur et al., Nanocapsule technology: a review, Crit Rev Ther Drug Carrier Syst. 2002;19(2):99-134.
Deleve; Kaplowitz, "Glutathione metabolism and its role in hepatotoxicity" Pharm. Ther. vol. 52, 1991, pp. 287-305.
Demirci et al., Enhanced organically bound selenium yeast production by fed-batch fermentation, J Agric Food Chem. Jun. 1999;47(6):2496-500.
Demirci et al., Production of organically bound selenium yeast by continuous fermentation, J Agric Food Chem. Jun. 1999;47(6):2491-5.
Discher et al. Journal of Physical Chemistry B (2002), 106(11), 2848-2854.
El-Bayoumy, K. (1991) The role of selenium in cancer prevention. In: Cancer Principles and Practice of Oncology (DeVita, V. T., Hellman, S. & Rosenberg, S. S., eds.), 4th ed., pp. 1-15. J. B. Lippincott, Philadelphia, PA.
Ferris G. M. Lloyd et al. "The effect of supplementation with selenium and vitamin E in psoriasis" App. Clin. Biochem. vol. 26, 1989, pp. 83-88.
Furnsinn et al., "Improved glucose tolerance by acute vanadate but not by selenate exposure in genetically obese rats (fa/fa)" Int. J of Obesity and Related Metab. Dis. vol. 19, No. 7, 1995, pp. 458-463.
Garland et al., "Antioxidant micronutrients and breast cancer" J. Am. Coll Nutr. vol. 12, 1993, pp. 400-411.
Gerloff et al., "Effect of selenium supplementation on dairy cattle" J. Anim. Sci. vol. 70, 1992, pp. 3934-3940.
Ghadirian et al., "A case-control study of toenail selenium and cancer of the breast, colon, and Prostate" Cancer Detect Prev vol. 24, 2000, pp. 305-313.
Ghoroghchian et al., Bioresorbable Vesicles Formed through Spontaneous Self-Assembly of Amphiphilic Poly(ethylene oxide)-block-polycaprolactone, Macromolecules. Mar. 7, 2006;39(5)1673-1675.
Goehring et al., Effects of seleniferous grains and inorganic selenium on tissue and blood composition and growth performance of rats and swine, J Anim Sci. Sep. 1984;59(3):725-32.
Ip; Daniel, "Effects of selenium on 7,12-dimethylbenz(a)anthracene-induced mammary carcinogenesis and DNA adduct formation" Cancer Res. vol. 45, 1985, pp. 61-65.
Ip, "Lessons from basic research in selenium and cancer prevention" J. Nutr. vol. 128, 1998, pp. 1845-1854.
Kelly, M. P.; Power R. F. 'Fractionation and identification of the major selenium compounds in selenized yeast' J. Dairy Sci. 78, 237-242 (1995).

(Continued)

*Primary Examiner* — Suzanne M Noakes
(74) *Attorney, Agent, or Firm* — Casimir Jones, S.C.

(57) ABSTRACT

The invention relates to soluble selenium compositions and methods of production, separation and purification thereof. In particular the present invention provides methods of preparing water soluble selenoglycoproteins (e.g., via extracting selenoglycoproteins from selenium enriched yeast), methods of supplementing a selenium deficient composition via admixing water soluble selenoglycoproteins with the selenium deficient composition, compositions comprising the water soluble selenoglycoproteins and methods of administering the same.

17 Claims, 10 Drawing Sheets

OTHER PUBLICATIONS

Korhola.M.; Vainio, A.; Edaelman, K. 'Selenium yeast' Ann. Clin. Res. 18, 65-68, (1986).

Mahan, D.C. 1999. Organic selenium: using nature's model to redefine selenium supplementation for animals. In: Biotechnology in the Feed Industry. Proc. 15th Annual Symposium (T.P. Lyons and K.A. Jacques, eds.). Nottingham University Press, Nottingham, UK, pp. 523-535.

McKenzie, R.C.; Rafferty, T.S.; Beckett, G.J. 'Selenium: an essential element for immune function' Trends in Immunology 19, 342-345 (1998).

McSheehy, S.; Kelly, J.; Tessier, L.; Mester, Z. 'Identification of Selenomethionine in selenized yeast using two-dimentional liquid chromatography-mass spectrometry based proteomic analysis' Analyst 130, 35-37 (2005).

Meister; Anderson, Glutathione, Annual Review of Biochemistry, vol. 52: 711-760 (volume publication date Jul. 1983).

Mosbach. Trends in Biochemical Sciences, vol. 7, pp. 92-96, 1994.

Otero, M.A.; Vasallo, M.C.; Verdecia, O.; Fernandez, V.; Betancourt, D. 'A Process for the Complete Fractionation of Baker's Yeast' J. Chem. Tech. Biotechnol. 66, 67-71 (1996).

Ouerdane L., Mester Z. 'Production and Characterization of Fully Selenomethionine-Labelled *Saccharomyces cerevisiae*' J.Agric. Food Chem. 56,11792-11799, (2008).

Palmer; Paulson, "Reactive oxygen species and antioxidants in signal transduction and gene Expression" Nutr. Rev. vol. 55, 1997, pp. 353-361.

Pence et al., Effects of dietary selenium on UVB-induced skin carcinogenesis and epidermal antioxidant status, J Invest Dermatol. May 1994;102(5):759-61.

Rayman, The importance of selenium to human health, Lancet. Jul. 15, 2000;356(9225):233-41.

Roberge, M.T.; Borgerding, A.J.; Finley, J.W. 'Speciation of Selenium Compounds from High Selenium Broccoli Is Affected by the Extracting Solution' J.Agric. Food Chem. 51, 4191-4197 (2003).

Salonen et al., "Association between serum selenium and the risk of cancer" Am. J. Epidemiol. vol. 120, 1984, pp. 342-349.

Surai P.F. Natural Antooxidants in Avian Nutrition and Reproduction Nottingham University Press 2002, 234-236 (2002).

Tapiero, H.; Townsend, D.M.; Tew, K.D. 'The antioxidant role of selenium and selenocompounds' Biomedicine&Pharmacotherapy 57, 134-144 (2003).

Virtamo et al., "Serum selenium and risk of cancer. A prospective follow-up of nine years" Cancer vol. 60, 1987, pp. 145-148.

Willett et al., "Prediagnostic serum selenium and risk of cancer" Lancet vol. 2, 1983, pp. 130-134.

Wulff, The role of binding-site interactions in the molecular imprinting of polymers, Trends Biotechnol. Mar. 1993;11 (3):85-7.

Yoshizawa et al., "Study of prediagnostic selenium level in toenails and the risk of advanced prostate cancer" J Natl Cancer Inst vol. 90, 1998, pp. 1219-1224.

Yu et al., "Protective role of selenium against hepatitis B virus and primary liver cancer in Qidong" Biol Trace Elem Res vol. 56, 1997, pp. 117-124.

Andersson et al., Mimics of the binding sites of opioid receptors obtained by molecular imprinting of enkephalin and morphine, Proc. Natl. Acad. Sci., vol. 92, pp. 4788-4792, May 1995.

\* cited by examiner

METHODS FOR SEPARATING SOLUBLE SELENOGLYCOPROTEINS

This Application claims priority to U.S. Provisional Patent Application Ser. No. 61/315,265 filed Mar. 18, 2010, hereby incorporated by reference in its entirety.

FIELD OF THE INVENTION

The present invention relates to soluble selenium compositions and methods of production, separation and purification thereof. In particular the present invention provides methods of preparing water soluble selenoglycoproteins (e.g., via extracting selenoglycoproteins from selenium enriched yeast), methods of supplementing a selenium deficient composition via admixing water soluble selenoglycoproteins with the selenium deficient composition, compositions comprising the water soluble selenoglycoproteins and methods of administering the same.

BACKGROUND OF THE INVENTION

Selenium is a trace element important for proper physiological function in humans. Selenium is ingested through the diet which can have a varying content of selenium.

Selenium is known to play a critical role in sustaining physiologic metabolism, growth, reproductive health, and immunity. Selenium is incorporated into different organic molecules including, for example, amino acids such as 1-selenomethionine, selenocysteine, and selenocystine. Thus, selenium can be a component part of proteins, many of which are of structural importance to the body. Furthermore, selenium is an important ingredient in a number of enzymes which influence metabolism, reproduction, the prevention of cancer, and immune defense in humans (See, e.g., Rayman, M, Lancet 356:233-241 (2000)).

Multiple studies have attempted to reveal potential health benefits resulting from the ingestion of low levels of selenium. For example, low concentrations of an inorganic form of selenium, have shown some potential health benefits (See, e.g., Furnsinn et al., Int. J of Obesity and Related Metab. Dis., 19, 458-463 (1995)). However, at elevated dosage levels, beneficial effects are reversed and dangerous toxicity is manifested.

Research over the last two decades has suggested that selenium is effective in the reduction of cancer incidence when provided to animals at doses only 5- to 10-fold above nutritional requirement (See, e.g., El-Bayoumy, The role of selenium in cancer prevention, Philadelphia, Lippincott, 1-15, 1991). Chemoprevention studies with selenium in animal model systems have indicated that this element is effective for most, if not all of the organ systems and is protective against carcinogenic effects (See, e.g., El-Bayoumy, The role of selenium in cancer prevention, Philadelphia, Lippincott, 1-15, 1991. Both epidemiological studies and supplementation trials have also supported its efficacy in lowering the incidence of cancers of the liver, colon, prostate and lung (See, e.g., Yu et al. Biol Trace Elem Res, 56: 117-124 (1997); Clark et al., J Am Med Assoc, 276: 1957-1963 (1996); Yoshizawa et al., J Natl Cancer Inst, 90: 1219-1224, (1998); Brooks, et al., J Urol, 166: 2034-2038, (2001)). Other studies have demonstrated no beneficial effect for selenium reduction of cancers (See, e.g., Garland et al., J. Am. Coll Nutr., 12: 400-11 (1993); Ghadirian et al., Cancer Detect Prev, 24: 305-13 (2000)).

Multiple forms of selenium have been examined. These include inorganic selenium such as sodium selenite, and organic sources, including selenium yeast. There is a significant difference between toxicity of inorganic and organic selenium, the inorganic compounds usually being absorbed and utilized less efficiently and also being more toxic than organic sources of selenium.

SUMMARY OF THE INVENTION

The present invention relates to soluble selenium compositions and methods of production, separation and purification thereof. In particular the present invention provides methods of preparing water soluble selenoglycoproteins (e.g., via extracting selenoglycoproteins from selenium enriched yeast), methods of supplementing a selenium deficient composition via admixing water soluble selenoglycoproteins with the selenium deficient composition, compositions comprising the water soluble selenoglycoproteins and methods of administering the same.

Accordingly, in some embodiments, the present invention provides a method for preparation of soluble selenoglycoproteins comprising: providing selenium enriched yeast, exposing the selenium enriched yeast to acidic conditions followed by centrifugation to generate i) a pellet comprising acid insoluble material; and ii) a liquid phase comprising the extract of selenium enriched yeast soluble under the acidic conditions; precipitating selenoglycoproteins from the liquid phase comprising the extract of selenium enriched yeast soluble under the acidic conditions via raising the pH of the liquid phase, and (d) separating the precipitated selenoglycoproteins from the liquid phase. In some embodiments, exposing the selenium enriched yeast to acidic conditions occurs at a temperature greater than room temperature (e.g., greater than about 20-25° C.). The present invention is not limited by the temperature greater than room temperature under which the selenium enriched yeast are exposed to acidic conditions. Indeed, a variety of temperatures may be used including, but not limited to, about 30, 35, 40, 45, 50, 55, 60, 65, 70, 75, 80, 85, 90, 90, 95, 97, 99° C., or hotter). Similarly, the invention is not limited by the acidic conditions under which the selenium enriched yeast are exposed. In some embodiments, the selenium enriched yeast are exposed to conditions wherein the pH is about 6.5, about 6, about 5.5, about 5, about 4.5, about 4, about 3.5, about 3, about 2.5, about 2, about 1.5, about 1, or less. In a preferred embodiment, exposing the selenium enriched yeast to acidic conditions comprises exposure of the selenium enriched yeast to a pH of 1.5. In some embodiments, exposing the selenium enriched yeast to acidic conditions takes place for a certain period of time. The invention is not limited by the amount of time under which the selenium enriched yeast are exposed to acidic conditions. In some embodiments, the selenium enriched yeast are exposed to acidic conditions for about 1, 2, 3, 4, 5, 6, 7, 8, 9, 10, 11, 12, 14, 16, 18, 20, 22, 24 or more hours. In some embodiments, the selenium enriched yeast are exposed to acidic conditions for between one and twenty-four hours. In some embodiments, the selenium enriched yeast are exposed to acidic conditions for between five and ten hours. In a preferred embodiment, the selenium enriched yeast are exposed to acidic conditions for about eight hours. In some embodiments, acidic conditions are created and/or maintained utilizing acidic buffer and/or the addition of an acid. The invention is not limited by the type of acid utilized. Indeed, any acid may be used. In some embodiments, the acid is hydrochloric acid, although any acid may be used. In some embodiments, selenoglycoproteins are precipitated from the liquid phase comprising the extract of selenium enriched yeast soluble under the acidic conditions via raising the pH of the liquid phase. In some embodiments, the precipitated selenoglycoproteins are separated from the liquid phase via centrifugation to form a pellet of the precipitated selenoglycoproteins followed by removal of the liquid phase from the precipitated selenoglycoproteins. The invention is not limited by the amount or degree to which the pH of the extract is raised in order to precipitate the selenoglycoproteins from the liquid phase. In some embodiments, the pH of the liquid phase is raised to 1.85. In some embodiments, the pH of the liquid phase is raised to 3.0. In some embodiments, the pH of the liquid phase is raised to 4.0. In some embodiments, the pH of the liquid phase is raised to 6.0. In some embodiments, selenoglycoproteins are precipitated and separated from the liquid phase at a variety of pH conditions to generate multiple pH dependent fractions of soluble selenoglycoproteins. For example, in some embodiments, a single liquid phase comprising the extract of selenium enriched yeast soluble under acidic conditions is used to create a first fraction of soluble selenoglycoproteins precipitated at a first pH (e.g., pH of 1.85), a second fraction of soluble selenoglycoproteins precipitated at a second pH (e.g., pH of 3.0), a third fraction of soluble selenoglycoproteins precipitated at a third pH (e.g., pH of 4.0), and a fourth fraction of soluble selenoglycoproteins precipitated at a fourth pH (e.g., pH of 6.0). In some embodiments, precipitating the selenoglycoproteins from the liquid phase via raising the pH of the liquid phase comprises multiple, sequential pH dependent precipitation reactions of the liquid phase. In some embodiments, a composition comprising soluble selenoglycoproteins contains only a single, pH dependent fraction of the selenoglycoproteins (e.g., soluble selenoglycoproteins from liquid phase comprising the extract of selenium enriched yeast soluble under acidic conditions precipitated at pH 4.0). In some embodiments, a composition comprising soluble selenoglycoproteins contains two or more pH dependent fractions of selenoglycoproteins (e.g., soluble selenoglycoproteins from liquid phase comprising the extract of selenium enriched yeast soluble under acidic conditions precipitated at two or more different pH values). In some embodiments, the selenium enriched yeast are dried, nonviable selenium-enriched yeast containing 2% or less inorganic selenium.

The invention also provides compositions comprising soluble selenoglycoproteins prepared according to the invention. For example, in some embodiments, the invention provides a selenium deficient composition comprising soluble selenoglycoproteins of the invention. In some embodiments, soluble selenoglycoproteins of the invention are added to and/or mixed with a selenium deficient composition. The invention is not limited by the type of selenium deficient composition or material to which soluble selenoglycoproteins of the invention are added to or mixed with, such compositions or materials including, but not limited to, dietary supplements, drugs, pharmaceuticals, foodstuffs, animal feeds, and other types of materials. In some embodiments, adding or mixing (e.g., admixing) selenoglycoprotein comprises admixing selenoglycoprotein and one or more other types of selenium into the composition. In some embodiments, soluble selenoglycoproteins of the invention are added to and/or mixed with compositions that contain selenium (e.g., to augment and/or supplement the total amount of selenium).

The invention also provides a composition comprising soluble selenoglycoproteins and a carrier. In some embodiments, the selenoglycoproteins are a specific pH dependent fraction of selenoglycoproteins. The invention is not limited by the type of carrier utilized. Indeed a variety of carriers may be used including, but not limited to, dendrimers, polymerosomes, nanoparticles, slow-release polymers, nanocapsules, and/or molecularly imprinted polymers. In one preferred embodiment, the carrier is a slow-release polymer. In another preferred embodiment, the carrier is a molecularly imprinted polymer. In still another preferred embodiment, the carrier is a polymersome used to encapsulate selenoglycoprotein. The invention is not limited by the type of polymersome used. Indeed, any polymersome known in the art may be utilized. In some embodiments, the polymersome comprises poly(ethylene oxide) (PEO) block copolymer. However, the invention is not so limited. Any known block copolymer may be utilized, including, for example poly(ethylethylene) (PEE), poly(butadiene) (PB or PBD), poly(styrene) (PS), and poly(isoprene) (PI). In some embodiments, the polymer comprises poly(ε-caprolactone) (PCL) diblock co-polymer. In some embodiments, the polymersome comprises poly(ethylene oxide)-block-poly(ε-caprolactone) (PEO-b-PCL) based diblock copolymers. In some embodiments, the polymersome comprises a block copolymer that is a triblock, tetrablock, pentablock, or at least six block copolymer. In some embodiments, the polymersome is derived from the coupling of poly(lactic acid), poly(glycolide), poly(lactic-coglycolic acid) and/or or poly(3-hydroxybutyrate) with PEO. The invention is not limited by the size of a polymersome encapsulated selenoglycoprotein. A variety of sizes find use in the compositions and methods of the invention including, but not limited to, polymersome encapsulated selenoglycoproteins that are about, 50-300 nm in diameter although larger (e.g., about 350 nm, 400 nm, 500 nm or larger) and smaller (e.g., about 40 nm, 30 nm. 20 nm, or smaller) polymersome encapsulated selenoglycoproteins may be used.

DEFINITIONS

Figure 1:
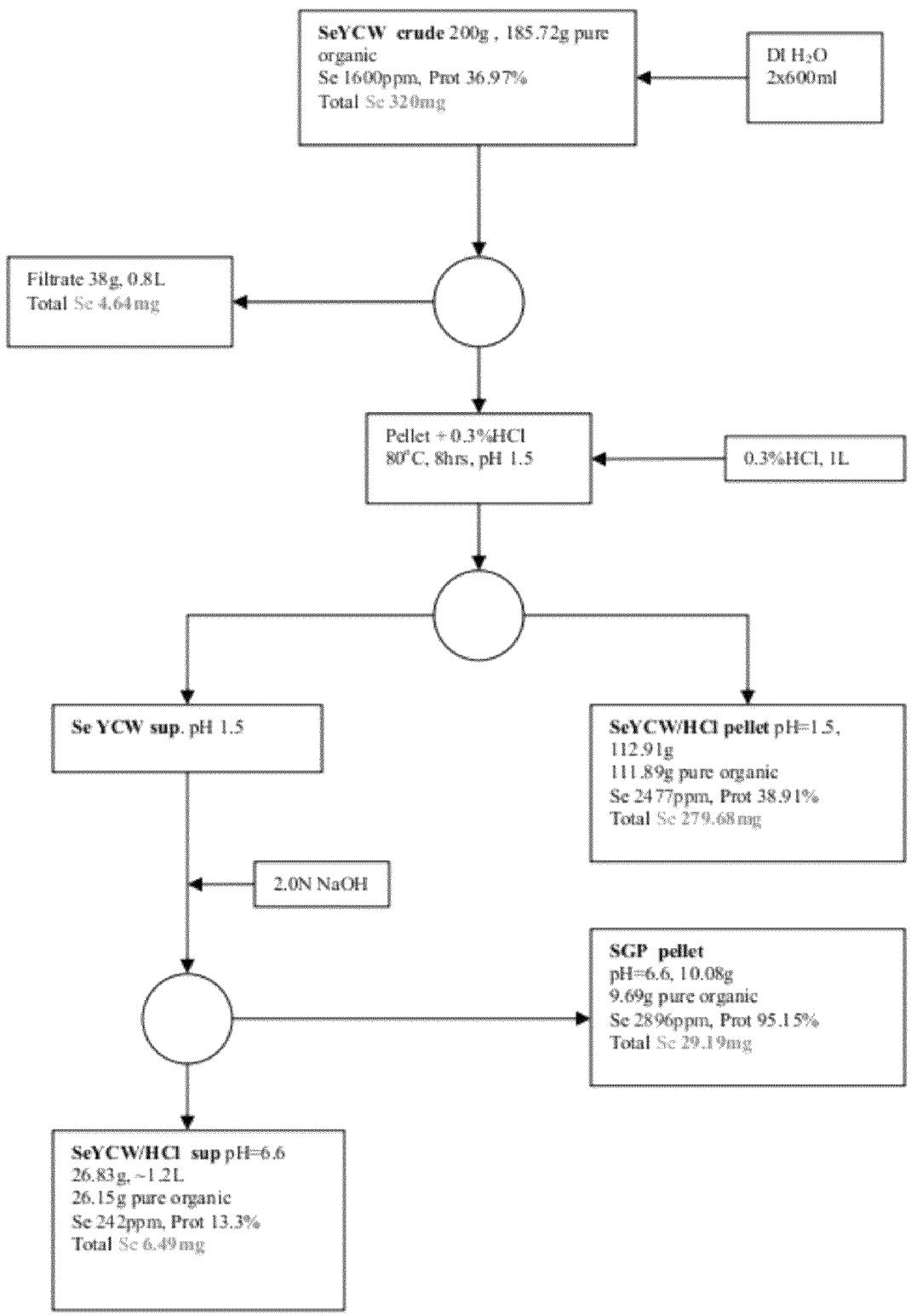
FIG. 1 shows a schematic of an embodiment of the present invention.

To facilitate an understanding of the present invention, a number of terms and phrases are defined below:

As used herein, the terms "peptide," "polypeptide" and "protein" all refer to a primary sequence of amino acids that are joined by covalent "peptide linkages." In general, a peptide consists of a few amino acids, typically from 2-50 amino acids, and is shorter than a protein. The term "polypeptide" encompasses peptides and proteins.

The term "glycoprotein(s)" or "glycopeptides(s)" refers to a protein or peptide which contains one or more carbohydrate residues covalently attached to the polypeptide chain. The term "selenoprotein(s)" or "selenopeptide(s)" refers to a protein or peptide which contains one or more selenium atoms. Typically, selenium atoms are incorporated into proteins within selenuim-containing amino acids including selenocysteine and selenomethionine.

The term "selenoglycoprotein(s)," "selenoglycopeptide(s)" or "SGP(s)" refers to a glycoprotein or glycopeptides which incorporate one or more selenium atoms. Typically, "selenoglycoproteins" comprise one or more selenium-containing amino acids. "Selenoglycoproteins" may comprise a number of carbohydrates in any number of different forms.

The terms "sample" and "specimen" are used in their broadest sense and encompass samples or specimens obtained from any source. As used herein, the term "sample" is used to refer to biological samples obtained from animals (including humans), and encompasses fluids, solids and tissues. In some embodiments of this invention, biological samples include cerebrospinal fluid (CSF), serous fluid, urine and saliva, blood, and blood products such as plasma, serum and the like. However, these examples are not to be construed as limiting the types of samples that find use with the present invention.

As used herein, the term "yeast" and "yeast cells" refers to eukaryotic microorganisms classified in the kingdom Fungi, having a cell wall, cell membrane and intracellular components. Yeasts do not form a specific taxonomic or phylogenetic grouping. Currently about 1,500 species are known; it is estimated that only 1% of all yeast species have been described. The term "yeast" is often taken as a synonym for *S. cerevisiae*, but the phylogenetic diversity of yeasts is shown by their placement in both divisions *Ascomycota* and *Basidiomycota*. The term "yeast" encompasses brewer's yeast, distillers yeast and Baker's yeasts. The budding yeasts ("true yeasts") are classified in the order Saccharomycetales. Most species of yeast reproduce asexually by budding, although some reproduce by binary fission. Yeasts are unicellular, although some species become multicellular through the formation of a string of connected budding cells known as pseudohyphae, or false hyphae. Yeast size can vary greatly depending on the species, typically measuring 3-4 µm in diameter, although some yeast can reach over 40 µm.

As used herein, the terms "selenium-enriched yeast" and "selenized yeast" refer to any yeast (e.g., *Saccharomyces cerevisiae*) that is cultivated in a medium containing inorganic selenium salts. The present invention is not limited by the selenium salt used. Indeed, a variety of selenium salts are contemplated to be useful in the present invention including, but not limited to, sodium selenite, or sodium selenate. Free selenomethionine (e.g., not associated with a cell or yeast) can also be used as the selenium source for selenium enriched yeast as yeast does incorporate this form of selenium. During cultivation, because of the chemical similarity between selenium and sulfur, yeast incorporate selenium in place of sulfur in what are normally sulfur-containing organic compounds within the cell. A selenium-containing compound in such yeast preparations is selenomethionine that is incorporated into polypeptides/proteins. The amount of total cellular selenium present in the form of selenomethionine in such preparations will vary, but can be between 10 and 100%, 20-60%, 50-75% and between 60 and 75%. The remainder of the organic selenium in selenized yeast preparations is predominantly made up of intermediates in the pathway for selenomethionine biosynthesis. These include, but are not limited to, selenocysteine, selenocystathionine, selenohomocysteine and seleno-adenosylselenomethionine. The amount of residual inorganic selenium salt in the finished product is generally quite low (e.g., <2%).

As used herein, the term "SEL-PLEX" refers to a dried, nonviable selenium-enriched yeast (e.g. *Sacchoromyces cerevisiae* of accession number CNCM I-3060, Collection Nationale De Cultures De Microorganismes (CNCM), Institut Pasteur, Paris, France) cultivated in a fed-batch fermentation that provides incremental amounts of cane molasses and selenium salts in a manner that minimizes the detrimental effects of selenium salts on the growth rate of the yeast and allows for optimal incorporation of inorganic selenium into cellular organic material. Residual inorganic selenium is eliminated (e.g., using a rigorous washing process) and does not exceed 2% of the total selenium content.

As used herein, the term "organic selenium" refers to any organic compound wherein selenium atom is directly connected to a carbon atom.

As used herein, the term "inorganic selenium" generally refers to any selenium salt (e.g., sodium selenite, sodium selenate) in which selenium is at -2, +4 and +6 oxidation state.

As used herein, the terms "host," "subject" and "patient" refer to any animal, including but not limited to, humans and animals (e.g., primates, dogs, cats, cows, horses, sheep, poultry, fish, crustaceans, etc.) that is studied, analyzed, tested, diagnosed or treated. As used herein, the terms "host," "subject" and "patient" are used interchangeably, unless indicated otherwise.

As used herein, the term "w/w" ("weight/weight") refers to the amount of a given substance in a composition on weight basis. For example, an animal feed comprising 0.02% w/w dietary feed supplement means that the mass of the dietary feed supplement is 0.02% of the total mass of the animal feed (e.g., 200 grams of dietary feed supplement composition in 999,800 grams of animal feed).

As used herein, the term "purified" or "to purify" refers to the removal of components from a sample. For example, yeast cell walls are purified by removal of non-yeast cell wall components (e.g., plasma membrane and/or yeast intracellular components); they are also purified by the removal of contaminants or other agents other than yeast cell wall. The removal of non-yeast cell wall components and/or non-yeast cell wall contaminants results in an increase in the percent of yeast cell wall or components thereof in a sample.

As used herein, the term "effective amount" refers to the amount of a composition (e.g., comprising selenoglycoproteins of the present invention sufficient to effect beneficial or desired results. An effective amount can be administered in one or more administrations, applications or dosages and is not intended to be limited to a particular formulation or administration route.

As used herein, the term "bioavailability" refers to the fraction of a molecule or component that is available to an organism or reaches the systemic circulation. When a molecule or component is administered intravenously, its bioavailability is quite high. However, when a molecule or component is administered via other routes (such as orally), its bioavailability decreases (due to incomplete absorption and first-pass metabolism). In a nutritional setting, bioavailability refers to the rates of absorption and utilization of a nutrient. Different forms of the same nutrient, for example, may have different bioavailabilities.

As used herein, the terms "feed", "foodstuffs", "animal feed", and "feedstuffs" refer to material(s) that are consumed by animals and contribute energy and/or nutrients to an animal's diet. Examples include, but are not limited to, Total Mixed Ration (TMR), forage(s), pellet(s), concentrate(s), premix(es) coproduct(s), grain(s), distiller grain(s), molasses, fiber(s), fodder(s), grass(es), hay, kernel(s), leaves, meal, soluble(s), and supplement(s).

As used herein, the terms "food supplement," "dietary supplement," "dietary supplement composition," and the like refer to a food product formulated as a dietary or nutritional supplement to be used as part of a human or animal diet, e.g. as an addition to animal feed.

As used herein, the terms "administration" and "administering" refer to the act of giving a drug, prodrug, or other agent, or therapeutic treatment (e.g., compositions of the present invention) to a subject (e.g., a subject or in vivo, in vitro, or ex vivo cells, tissues, and organs). Exemplary routes of administration to the human body can be through the eyes (ophthalmic), mouth (oral), skin (topical or transdermal), nose (nasal), lungs (inhalant), oral mucosa (buccal), ear, rectal, vaginal, by injection (e.g., intravenously, subcutaneously, intratumorally, intraperitoneally, etc.) and the like.

As used herein, the terms "co-administration" and "co-administering" refer to the administration of at least two agent(s) (e.g., composition comprising selenoglycoproteins of the invention and one or more other agents—e.g., an antibiotic, a therapeutic (e.g., drug or pharmaceutical), or, other biologically active compound) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

As used herein, the term "treatment" or grammatical equivalents encompasses the improvement and/or reversal of the symptoms of disease (e.g., neurodegenerative disease). A compound which causes an improvement in any parameter associated with disease when used in the screening methods of the instant invention may thereby be identified as a therapeutic compound. The term "treatment" refers to both therapeutic treatment and prophylactic or preventative measures. For example, those who may benefit from treatment with compositions and methods of the present invention include those already with a disease and/or disorder (e.g., neurodegenerative disease, diabetes or lack of or loss of cognitive function) as well as those in which a disease and/or disorder is to be prevented (e.g., using a prophylactic treatment of the present invention).

As used herein, the term "at risk for disease" refers to a subject (e.g., a human) that is predisposed to experiencing a particular disease. This predisposition may be genetic (e.g., a particular genetic tendency to experience the disease, such as heritable disorders), or due to other factors (e.g., age, weight, environmental conditions, exposures to detrimental compounds present in the environment, etc.). Thus, it is not intended that the present invention be limited to any particular risk, nor is it intended that the present invention be limited to any particular disease.

As used herein, the term "suffering from disease" refers to a subject (e.g., a human) that is experiencing a particular disease. It is not intended that the present invention be limited to any particular signs or symptoms, nor disease. Thus, it is intended that the present invention encompass subjects that are experiencing any range of disease (e.g., from sub-clinical manifestation to full-blown disease) wherein the subject exhibits at least some of the indicia (e.g., signs and symptoms) associated with the particular disease.

As used herein, the terms "disease" and "pathological condition" are used interchangeably to describe a state, signs, and/or symptoms that are associated with any impairment of the normal state of a living animal or of any of its organs or tissues that interrupts or modifies the performance of normal functions, and may be a response to environmental factors (such as radiation, malnutrition, industrial hazards, or climate), to specific infective agents (such as worms, bacteria, or viruses), to inherent defect of the organism (such as various genetic anomalies), or to combinations of these and other factors.

The term "compound" refers to any chemical entity, pharmaceutical, drug, and the like that can be used to treat or prevent a disease, illness, sickness, or disorder of bodily function. Compounds comprise both known and potential therapeutic compounds. A compound can be determined to be therapeutic by screening using the screening methods of the present invention. A "known therapeutic compound" refers to a therapeutic compound that has been shown (e.g., through animal trials or prior experience with administration to humans) to be effective in such treatment. In other words, a known therapeutic compound is not limited to a compound efficacious in the treatment of disease (e.g., cancer, neurodegenerative disease, etc.).

As used herein, the term "kit" is used in reference to a combination of reagents and other materials. It is contemplated that the kit may include reagents such as nutrients and drugs as well as administration means. It is not intended that the term "kit" be limited to a particular combination of reagents and/or other materials.

As used herein, the term "toxic" refers to any detrimental or harmful effects on a subject, a cell, or a tissue as compared to the same cell or tissue prior to the administration of the toxicant.

As used herein, the term "pharmaceutical composition" refers to the combination of an active agent (e.g., composition comprising selenoglycoproteins) with a carrier, inert or active, making the composition especially suitable for diagnostic or therapeutic use in vitro, in vivo or ex vivo.

The terms "pharmaceutically acceptable" or "pharmacologically acceptable," as used herein, refer to compositions that do not substantially produce adverse reactions, e.g., toxic, allergic, or immunological reactions, when administered to a subject.

As used herein, the term "topically" refers to application of the compositions of the present invention to the surface of the skin and mucosal cells and tissues (e.g., alveolar, buccal, lingual, masticatory, or nasal mucosa, and other tissues and cells that line hollow organs or body cavities).

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintrigrants (e.g., potato starch or sodium starch glycolate), and the like. The compositions also can include stabilizers and preservatives. Examples of carriers, stabilizers and adjuvants are described, for example, in ee e.g., Martin, Remington's Pharmaceutical Sciences, 15th Ed., Mack Publ. Co., Easton, Pa. (1975), incorporated herein by reference).

As used herein, the term "pharmaceutically acceptable salt" refers to any salt (e.g., obtained by reaction with an acid or a base) of a compound of the present invention that is physiologically tolerated in the target subject (e.g., a mammalian subject, and/or in vivo or ex vivo, cells, tissues, or organs). "Salts" of the compounds of the present invention may be derived from inorganic or organic acids and bases. Examples of acids include, but are not limited to, hydrochloric, hydrobromic, sulfuric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts. Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like. Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, methanesulfonate, 2-naphthalenesulfonate, nicotinate, oxalate, palmoate, pectinate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

As used herein, the term "drying" refers to spray drying, freeze drying, air drying, vacuum drying or any other kind of process that reduces or eliminates liquid in a substance.

As used herein, the term "spray drying" refers to a commonly used method of drying a substance containing liquid using hot gas to evaporate the liquid to reduce or eliminate liquid in the substance. In other words the material is dried by way of spraying or atomizing into a draft of heated dry air.

As used herein, the term "freeze-drying" and the term "lyophilization" and the term "cryodesiccation" refer to the removal of a solvent from matter in a frozen state by sublimation. This is accomplished by freezing the material to be dried below its eutectic point and then providing the latent heat of sublimation. Precise control of vacuum and heat input permits drying from the frozen state without product melt-back. In practical application, the process is accelerated and precisely controlled under reduced pressure conditions.

As used herein, the term "dry free flowing powder" refers to a free flowing dry powder, e.g. a powder that can be poured from a container, bag, vessel etc without hindrance of large clumps.

As used herein, the term "grinding" refers to reducing particle size by impact, shearing, or attrition.

As used herein, the term "washing" refers to the removal or cleansing (e.g., using any type of solute (e.g. distilled water, buffer, or solvent) or mixture) of impurities or soluble unwanted component of a preparation (e.g., a yeast cell wall) may be washed to remove non-yeast cell wall components from the sample).

As used herein, the term "polymersome" refers to vesicles that are assembled from synthetic polymers in aqueous solution (e.g., that can be utilized to encapsule a material). Polymersomes can be made using amphiphlic synthetic block copolymers to form the vesicle membrane, and have radii ranging from 50 nm to 5 μm or more. Most polymersomes contain an aqueous solution in their core and are useful for encapsulating and protecting sensitive molecules, such as drugs, enzymes, other proteins and petptides as well as DNA and RNA fragments. The polymersome membrane provides a physical barrier that isolates the encapsulated material from external materials, such as those found in biological systems. Examples of polymersomes that find use in embodiments of the invention, as well as their synthesis, can be found, for example, in U.S. Pat. Nos. 7,867,512, 7,682,603, and 6,835,394, each of which is hereby incorporated by reference in its entirety.

As used herein, the term "waste" refers to unwanted or useless materials.

As used herein, the term "wastewater" is any water that has been adversely affected in quality by anthropogenic influence.

DETAILED DESCRIPTION OF THE INVENTION

I. Introduction

Selenium is a trace element involved in regulating aspects of the antioxidant defense mechanism in all living tissues by interacting with the body's glutathione (GSH) and its major Se-containing antioxidant enzymes, glutathione peroxidase (GPX) and thioredoxin reductase (See, e.g., Goehring et al., J. Anim. Sci. 59, 725-732 (1984); Gerloff et al., J. Anim. Sci. 70, 3934-3940 (1992); herein incorporated by reference in their entireties). Glutathione and GPX have the capacity to protect the integrity of unsaturated bonds of membrane phospholipids by extinguishing free radical attacks capable of initiating and propagating lipid oxidation (See, e.g., Meister and Anderson, Annu Rev. Biochem. 52, 711-760 (1983); Deleve and Kaplowitz, Pharm. Ther. 52, 287-305 (1991); Palmer and Paulson, Nutr. Rev. 55, 353-361 (1997); herein incorporated by reference in their entireties).

Selenium has also been associated with reduced cancer risk in several epidemiologic studies (See, e.g., Salonen et al., Am. J. Epidemiol. 120: 342-349 (1984); Willett et al., Lancet 2:

130-134 (1983); Virtamo et al., Cancer 60: 145-148 (1987); herein incorporated by reference in their entireties). Various selenium compounds of natural and synthetic origin have been shown to inhibit tumor development in animal studies in a wide range of dosages (See, e.g., Ip, J. Nutr. 128: 1845-1854 (1998); herein incorporated by reference in its entirety). Although most animal studies have employed pharmacologic doses of selenium (>2 mg/kg) in cancer chemoprevention (See, e.g., Ip, J. Nutr. 128: 1845-1854 (1998)), selenium deficiency has also been shown to enhance mammary (See, e.g., Ip and Daniel, Cancer Res. 45: 61-65 (1985); herein incorporated by reference in its entirety) and UVB-induced skin carcinogenesis (See, e.g., Pence et al., 102: 759-761 (1994); herein incorporated by reference in its entirety).

Yeast cell wall proteins are connected to cell wall polysaccharides by chemical bond, and in order to release yeast cell wall protein into solution, these bonds need to be broken. The standard practice for protein extraction from yeast cell wall is to break the bonds using alkaline hydrolysis (pH 11.5, 80° C.) before centrifuging to separate proteins from glucan polysaccharides that are insoluble in water.

Experiments conducted during development of embodiments of the invention, were performed in an attempt to extract selenoglycoproteins using the standard practice of alkaline hydrolysis. These attempts to extract selenoglycoproteins from yeast cell wall using alkaline hydrolysis failed. It was later learned that the failure to extract selenoglycoproteins from yeast cell wall using alkaline hydrolysis is due to destruction of the selenoglycoproteins. Later attempts to extract selenoglycoproteins were conducted using a modified alkaline hydrolysis procedure (pH 11.5, 60° C.). These attempts also failed to extract selenoglycoproteins from yeast cell wall. The typical, alkaline, yeast protein extraction methods did not work when attempting to extract selenoglycoproteins from yeast. Thus, additional experiments were conducted during development of embodiments of the invention that attempted to extract selenoglycoproteins using an acidic extraction (pH 5, 80° C.). As described herein, the acidic extraction method was successful; the selenoglycoproteins were not destroyed and extraction was able to occur.

Thus, in some embodiments, the invention provides novel methods for obtaining selenoglycoproteins (SGPs), compositions comprising encapsulated selenoglycoproteins (SGP's), and methods of using the same (e.g., to provide in vivo benefit (e.g., changes in gene expression profiles) to a subject (e.g. human, animal, etc.)). In particular, experiments conducted during development of embodiments of the invention demonstrate that compositions (e.g., comprising SGP (e.g., isolated via a method of the invention)) and methods of the invention can be used to provide biologically available selenium to a subject (e.g., thereby increasing the selenium content of tissue and/or muscle within the subject (e.g., thereby leading to a stabilization and/or increase of the health of a subject))). In some embodiments, the invention provides methods for obtaining SGP's, compositions comprising encapsulated (e.g., polymersome encapsulated) SGP's and methods of using the same to alter cellular function (e.g., thereby providing beneficial effects to a system of a subject (e.g., including, but not limited to, musculoskeletal system, the neurological system, the nervous system, the endocrine system, the metabolic system, and/or the immune system). The invention also provides methods of using SGPs alone or in combination with one or more other active agents for treating or preventing disease. The invention also provides methods of using SGPs to enhance animal (e.g. livestock) health. In some embodiments, compositions of the invention are utilized to supplement, improve and/or enhance the health and/or nutritional value of food products (e.g. meat, dairy, eggs, etc.). In some embodiments, the invention provides compositions comprising SGPs and methods of using the same as a therapeutic, nutritional supplement, and/or prophylactic treatment (e.g., for general health, for boosting the immune system, for neurodegenerative disease, for enhancing cognitive function, etc.), and methods of making, producing, purifying, isolating, extracting, and/or characterizing the same. The invention also provides SGPs and methods of using SGPs for feeding animals and/or supplementing animal feed.

The invention also provides soluble selenium compositions (e.g. SGPs) and methods of use, production, and purification thereof. For example, in some embodiments, the invention provides separation and characterization of soluble SGPs (See, e.g., Examples 1-2), and compositions and methods for administration thereof (See, e.g., Examples 3-4). In some embodiments, the invention provides selenium (e.g. organic selenium) in a soluble form which can be administered to a subject through a variety of routes (e.g. oral, topical, intravenous, etc.). In some embodiments, the invention provides a low-fiber soluble selenium (e.g. organic selenium) composition. In some embodiments, the invention provides compositions and methods for soluble organic selenium delivery systems (e.g. polymersome encapsulated selenoglycoproteins, nanocapsules, polymers, etc.).

Yeast (e.g. *Saccharomyces cerevisiae*), grown in medium containing selenium (e.g. inorganic selenium (e.g. sodium selenite ($Na_2SeO_3$))) metabolize the selenium (e.g. inorganic selenium) and incorporate selenium instead of sulfur into cysteine and methionine, yielding proteins containing selenoaminoacids (SeCys and SeMet) (Demirci et al. J. Agric. Food Chem. 47, 2496-2500 (1999), Demirci & Pometto. J. Agric. Food Chem. 47, 2491-2495 (1999), Ouerdane & Mester. J. Agric. Food Chem. 56,11792-11799, (2008), each of which is herein incorporated by reference in their entireties). Alltech, Inc. (Nicholsville, Ky., USA) produces spray-dried selenium enriched yeast sold under the name of SEL-PLEX as a feed and food nutritional supplement, containing "organic selenium" (Korhola et al. Res. 18, 65-68, (1986), herein incorporated by reference in its entirety). The minimum concentration of selenium in SEL-PLEX is 1500 ppm and proteins are the exclusive carriers of it (See, e.g., Surai. Nottingham University Press 2002, 234-236 (2002), Kelly & Power. J. Dairy Sci. 78, 237-242 (1995), McSheehy et al. Analyst 130, 35-37 (2005), herein incorporated by reference in their entireties). There are two pools of proteins in yeast: proteins present inside of the yeast cell and proteins associated with the yeast cell wall mannan (See, e.g., Sedmak. US Patent Appl. Publication Pub. No.: US 2006/0263415, herein incorporated by reference in its entirety). About 17.0 weight % of commercial SEL-PLEX is soluble in water, and this material contains less than 6.5% of total selenium that is present in SEL-PLEX. Chicken feeding studies in which SEL-PLEX and sodium selenite were used as the sources of selenium, indicated much better selenium transfer into a chicken breast muscle by SEL-PLEX. A variety of bio-activities were discovered for oral administration of SEL-PLEX (See, e.g., Rayman. The Lancet 356, 233-241 (2000), McKenzie Trends in Immunology 19, 342-345 (1998), Tapiero. Biomedicine & Pharmacotherapy 57, 134-144 (2003), Combs & Grey Pharmacol. Ther. 79, 179-192 (1998), Clark et. al. J. Am. Med. Assoc. 276, 1957-1963 (1996), herein incorporated by reference in their entireties). Additional activities are contemplated for tissue-targeted, intravenous, or trans-dermal delivered active and soluble selenium components. In some embodiments, the invention provides separation, and physical and chemical characterization of soluble selenoglycoproteins (SGP's) from yeast (e.g. *Saccharomyces cerevisiae*) grown in medium containing selenium (e.g. inorganic selenium (e.g. sodium selenite)), and their active participation in "organic selenium" delivery to tissues (e.g. human, animal, chicken, etc.), by feeding the subject food (e.g. feed) supplemented with or otherwise containing SGP's of the invention (See, e.g. Examples 1-4). In some embodiments, the invention provides slow-release forms of "organic selenium" delivery systems (e.g. nanocapsules, polymer spheres, and polymersome encapsulated SGPs) (See, e.g. Examples 5-9). In some embodiments, the invention provides a composition comprising polymersome encapsulated SGP's. In some embodiments the invention provides enhanced delivery and improved biodistribution of SGP's by encapsulating SGP's inside poly(ethylene oxide)-block-poly (ε-caprolactone) (PEO-b-PCL) based polymersomes.

Separation of various yeast cell components by extracting cell wall from intracellular components of yeast cells has been described (See, e.g., Otero et al. J. Chem. Tech. Biotechnol. 66, 67-71 (1996), herein incorporated by reference in its entirety). These separation techniques have not been applied to the extraction of spray-dried selenium yeast. The conventional, alkaline conditions (pH 9.0-14.0) used in the art in extraction of glycoproteins from yeast (See, e.g., Roberge et. al. J. Agric. Food Chem. 51, 4191-4197 (2003), herein incorporated by reference in its entirety) failed because SeH or SeMe substituents were eliminated from selenocystine or selenomethionine amino acids. In other words, the desired substituents decomposed and as a result selenium that was present in the original SGP's was lost during attempted extraction in alkaline conditions when applied to extraction of yeast containing selenoproteins (See, e.g., Table 11 of Example 7).

Accordingly, in some embodiments, the invention provides selenoglycoprotein compositions (e.g., comprising a pH dependent fraction of selenoglycoproteins described herein) and methods of utilizing the same. In some embodiments, the invention provides methods of producing, purifying, isolating, extracting, separating, precipitating, and/or characterizing selenoglycoproteins (e.g. from selenium enriched yeast). In some embodiments, the invention provides compositions and methods for the delivery of soluble selenium compositions (e.g. SGPs) to a subject, including dietary supplement compositions (e.g. comprising SGPs (e.g., pharmaceuticals, nutriceuticals, supplements, foodstuffs, etc)). In some embodiments, the invention provides compositions and methods for advanced delivery (e.g. directed delivery, time-release delivery, etc.) of selenium (e.g. SGPs (e.g., polymersomes, nanocapsules, nanoparticles, polymers, etc.)). Compositions and methods of the invention might find use in a variety of applications including but not limited to dietary (e.g., admixing with feedstuffs or otherwise feeding to animals), therapeutic as well as research applications. Accordingly, in some embodiments, the invention provides animal feed compositions (e.g. comprising SGPs (e.g. soluble SGPs (e.g. soluble organic selenium))), methods of manufacturing the compositions and methods of providing nutrition (e.g. comprising SGPs (e.g. soluble SGPs (e.g. soluble organic selenium))) to animals comprising providing the compositions to the animals.

II. Extraction, Separation, Purification and Use

In some embodiments of the invention, soluble selenium is obtained in the form of selenoglycoproteins (SGPs). In some embodiments, SGPs are extracted from a general source of selenoproteins (e.g. selenium enriched yeast (e.g. SEL-PLEX)). In some embodiments, extraction and/or purification of SGPs comprises one or more pH-dependant extraction/precipitation steps (e.g., as described in Examples 1 and 2). In some embodiments, extraction and/or purification of SGPs comprises one or more pH-dependant fractionation steps. In some embodiments the invention provides acidic extraction of selenium enriched yeast (e.g. SEL-PLEX) to solubilize SGP's (e.g., without denaturing and/or destroying the SGPs). In some embodiments, the invention provides that pH-dependent precipitation of SGPs from an acidic extract (e.g., as described in Examples 1-2) produces increased content of selenoglycoproteins, decreased content of non-digestable fibers, and a high concentration of selenium (e.g., a concentration of selenium that is higher than that present in SEL-PLEX). Thus, in some embodiments, the invention provides SGP extracted from selenium enriched yeast wherein the selenium content of the SGP is greater than the selenium content of the material from which the SGP was extracted (e.g., in wt/wt %, ppm, etc.).

In some embodiments, SGPs are extracted from a general source of selenoproteins (e.g. selenium enriched yeast cells (e.g. SEL-PLEX)). In some embodiments, a portion of the selenoproteins in a selenoprotein source comprises SGPs (e.g. 0.1% . . . 0.2% . . . 0.5% . . . 1.0% . . . 2.0% . . . 5.0% . . . 10% . . . 20% . . . 50% or more SGPs). In some embodiments, a selenoprotein source comprises cells (e.g. yeast cells) which have been grown in the presence of Se-containing media (e.g. Se-rich media). In some embodiments, Se-containing cells (e.g. yeast cells) are processed to extract, isolate, and/or purify selenoproteins resulting in a selenoprotein source or selenoprotein-rich composition (e.g. SGP-rich composition). In some embodiments, a sample comprising selenoproteins and SGPs is enriched for SGPs.

In some embodiments, a selenoprotein source or selenoprotein-rich composition (e.g. selenium-enriched yeast source (e.g. SEL-PLEX)) is subjected to one or more steps to yield isolated, purified, separated, and/or extracted SGPs. In some embodiments, a selenoprotein source is mixed (e.g. in a liquid carrier (e.g. water, buffer, salt, etc.)) to produce a protein slurry, mixture, lysate, and/or solution. In some embodiments, the selenoprotein source (e.g. selenium-enriched yeast source (e.g. SEL-PLEX)) is mixed at high temperature (e.g. above freezing, above room temperature, 30° C. . . . 40° C. . . . 50° C. . . . 60° C. . . . 70° C. . . . 80° C. . . . 90° C. or higher). In some embodiments, the selenoprotein source (e.g., selenium-enriched yeast source (e.g. SEL-PLEX)) is mixed at low pH (e.g. acidic conditions (e.g. pH about 0.5, about 1.0, about 1.5, about 2.0, about 3.0, about 4.0, about 4.5, about 5.0, about 5.5, about 6.0 or about 6.5). In some embodiments, the selenoprotein source (e.g. selenium-enriched yeast source (e.g. SEL-PLEX)) is gently mixed, rapidly mixed, thoroughly mixed, vigorously mixed, etc. In some embodiments, the selenoprotein source (e.g., selenium-enriched yeast source (e.g. SEL-PLEX)) is mixed at low pH (e.g. acidic conditions (e.g. pH about 0.5, about 1.0, about 1.5, about 2.0, about 3.0, about 4.0, about 4.5, about 5.0, about 5.5, about 6.0 or about 6.5) and high temperature (e.g. above freezing, above room temperature, 30° C. . . . 40° C. . . . 50° C. . . . 60° C. . . . 70° C. . . . 80° C. . . . 90° C., or higher)). In some embodiments, the pH of the mixture is maintained through the addition of acid or base.

In some embodiments, the selenoprotein-containing mixture is centrifuged to separate the liquid/soluble and solid/insoluble phases. In some embodiments, a centrifuge speed is selected that is sufficient to separate the phases. In some embodiments, the liquid phase comprises soluble SGPs. In some embodiments, the pH of the liquid phase is adjusted (e.g. raised) to precipitate a portion of the SGPs. In some embodiments, the pH of the liquid fraction is raised slightly to moderately (e.g., pH raised by about 0.1 . . . 0.2 . . . 0.5 . . . 1.0 . . . 2.0) to precipitate SGPs which were soluble at the original pH, but not the elevated pH. In some embodiments, the pH of the liquid fraction is raised significantly (e.g., pH raised by about 1.0 . . . 2.0 . . . 3.0 . . . 4.0 . . . 5.0 . . . 6.0) to precipitate a large portion of the SGPs which were soluble at the original pH. In some embodiments, selenoglycoproteins are precipitated and separated from the liquid phase at a variety of pH conditions to generate multiple pH dependent fractions of soluble selenoglycoproteins. For example, in some embodiments, a single liquid phase comprising the extract of selenium enriched yeast soluble under acidic conditions is used to create a first fraction of soluble selenoglycoproteins precipitated at a first pH (e.g., pH of 1.85), a second fraction of soluble selenoglycoproteins precipitated at a second pH (e.g., pH of 3.0), a third fraction of soluble selenoglycoproteins precipitated at a third pH (e.g., pH of 4.0), and a fourth fraction of soluble selenoglycoproteins precipitated at a fourth pH (e.g., pH of 6.0). In some embodiments, precipitating the selenoglycoproteins from the liquid phase via raising the pH of the liquid phase comprises multiple, sequential pH dependent precipitation reactions of the liquid phase.

In some embodiments, precipitated SGPs are separated from the pH-adjusted liquid fraction by centrifugation (e.g. at sufficient speed to produce separate liquid and solid phases). In some embodiments, SGPs that have been separated from the liquid phase are freeze dried to yield a solid SGP fraction. In some embodiments, the process of raising the pH of the liquid phase and centrifuging to isolate the SGP fraction is repeated to produce SGP fractions of different solubility (e.g. soluble below pH 1.5 . . . soluble below pH 2 . . . soluble below pH 3 . . . soluble below pH 4 . . . soluble below pH 5 . . . soluble below pH 6, etc.). In some embodiments, a single pH adjustment and centrifugation steps are performed to produce one fraction containing SGPs of a desired solubility (e.g. soluble below pH 1.5. . . soluble below pH 2. . . soluble below pH 3 . . . soluble below pH 4 . . . soluble below pH 5 . . . soluble below pH 6, etc.). In some embodiments, the liquid phase that remains after removal of the final SGP fraction finds utility as a component of growth media for cells used in further production of selenoproteins or SGPs. In some embodiments, a composition comprising soluble selenoglycoproteins contains only a single, pH dependent fraction of the selenoglycoproteins (e.g., soluble selenoglycoproteins from liquid phase comprising the extract of selenium enriched yeast soluble under acidic conditions precipitated at pH 4.0). In some embodiments, a composition comprising soluble selenoglycoproteins contains two or more pH dependent fractions of selenoglycoproteins (e.g., soluble selenoglycoproteins from liquid phase comprising the extract of selenium enriched yeast soluble under acidic conditions precipitated at two or more different pH values).

Figure 2:
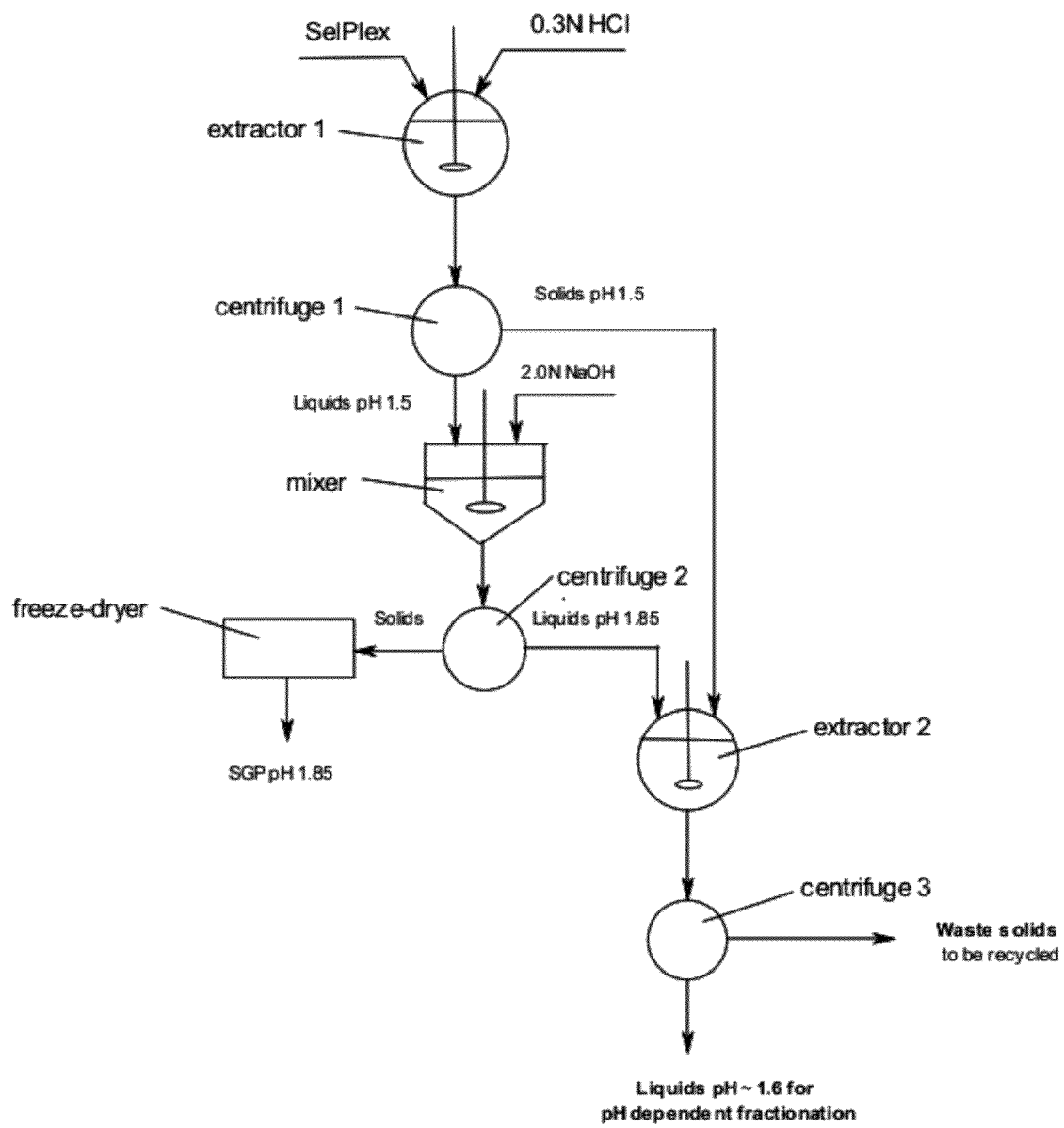
FIG. 2 shows a schematic of an embodiment of the present invention.

In a preferred embodiment, the process of SGP extraction from a selenoprotein source (e.g. selenium enriched yeast (e.g., SEL-PLEX)) and pH dependent fractionation of the mixture of SGP's (See, e.g., FIGS. 2 and 3) comprises two stages (See e.g., Examples 1-2, FIGS. 1 and 2). In the first stage, a suspension of selenium enriched yeast in 0.3N HCl (pH 1.5) is stirred and heated at 80° C. for 8 hrs. The pH of the mixture is maintained at pH1.5 by adding concentrated HCl during the first hour of the extraction. After eight hours, the mixture is centrifuged, and the liquid phase is separated. The pH of the solution is adjusted to 1.85, by the addition of 2.0N NaOH and SGP's that have limited solubility at this pH precipitate from the solution and are separated from the liquids (pH 1.85) by the second centrifugation and then freeze-dried to yield solid SGP fraction of pH 1.85. In some embodiments, the liquids (pH 1.85) are mixed with the solids (pH 1.5) from the first centrifugation, which results in change of the pH of the mixture to pH 1.6. The majority of the SGP's soluble at pH 1.6, are transferred into the liquid phase, without increasing the volumes of the waste streams created within this stage of the process. The major by-product from this stage of the process are solids from the second centrifugation. The stream of waste solids constitutes about 56.5 weight % of the selenium enriched yeast taken for extraction and contains valuable selenium yeast cell wall material containing: 38.91% of protein and 2477 ppm of selenium. In some embodiments, these solids are utilized (e.g., alone or in combination with other material (e.g., selenium enriched yeast)) as an environmentally friendly nutritional supplement in animal diets. In the second stage (See, e.g., FIG. 3), the liquid phase (pH 1.6) from the second centrifugation (SEE FIG. 2) is transferred to a mixer and the pH is adjusted to pH 3.0 by the addition of 2.0N NaOH and SGP's that have limited solubility at this pH precipitate from the solution and are separated from the liquids (pH 3.0) by the third centrifugation and finally freeze-dried to yield solid SGP fraction of pH 3.0 (See, e.g., Examples 1-2 and FIGS. 2 and 3). The liquid phase (pH 3.0) from the third centrifugation is transferred to a mixer and the pH adjusted to pH 4.0 by the addition of 2.0N NaOH and SGP's that have limited solubility at this pH precipitate from the solution and are separated from the liquids (pH 4.0) by the fourth centrifugation and finally freeze-dried to yield solid SGP fraction of pH 4.0. The liquid phase (pH 4.0) from the fourth centrifugation is transferred to a mixer and the pH is adjusted to pH 6.0 by the addition of 2.0N NaOH and SGP's that have limited solubility at this pH precipitate from the solution and are separated from the liquids (pH 6.0) by the fifth centrifugation and then freeze-dried to yield solid SGP fraction of pH 6.0. The only waste stream produced at the second stage of the process is the waste water stream, containing 13.4 weight % of solids (in comparison with the weight of selenium enriched yeast used in extraction) out of which the protein fraction constitutes about 13.3 weight %, sodium chloride for 3.6 weight % and glucose and mannose mono- and oligosaccharides constitute above 80 weight %. This "waste water" stream of pH 6.0 and selenium concentration of 242 ppm can be recycled or otherwise reused to the preparation of a new batch of selenium yeast (e.g. utilized in growth media).

In some embodiments, SGP's precipitated at pH 4.0 exhibit superior selenium delivery (e.g. to muscle tissue) as compared to selenium enriched yeast (e.g. SEL-PLEX) and far superior delivery when compared to inorganic forms of selenium (e.g. sodium selenite) (See, e.g. Example 3). Additionally, pH dependent selenoglycoprotein fractions (e.g., pH 6.0) are different compositionally than selenium enriched yeast (e.g., SEL-PLEX) and allow for delivery of similar amounts of selenium while requiring much less of the starting material (e.g., selenium enriched yeast).

In some embodiments, a SGP extraction procedure comprises 4 or fewer of the pH adjustment and centrifugation steps of the above procedure (e.g. 1 pH adjustment and centrifugation step, 2 pH adjustment and centrifugation steps, 3 pH adjustment and centrifugation steps, 4 pH adjustment and centrifugation steps).

III. Animal Feed

Animal feed refers to any foodstuff used to feed domesticated livestock (e.g., cattle, goats, sheep, horses, poultry, buffalo, alpaca, llamas, donkeys, mules, rabbits, chickens, geese, turkeys, or pigs). Animal feeds often include hay, straw, silage, compressed and pelleted feeds, oils and mixed rations, and also sprouted grains and legumes. The worldwide animal feed industry consumed 635 million tons of feed in 2006, with an annual growth rate of about 2%. The use of agricultural land to grow feed rather than human food can be controversial; some types of feed, such as corn (maize), can also serve as human food, while others such as grass cannot. In addition to providing an energy source to animals, animal feeds also provide nutrients (e.g. selenium) utilized by the body.

In some embodiments, the invention provides nutritional compositions (e.g. soluble selenium compositions (e.g. SGPs) that permit generation of animal feed compositions comprising selenium (e.g. elevated concentrations of selenium over standard feed compositions (e.g. soluble selenium)) that decreases overall costs, increases feed conversion and maintains and/or improves quality of animal products (e.g. meat, eggs, dairy, etc.) derived from livestock receiving the same compared to conventional animal feeds.

For example, in some embodiments, the invention provides a dietary supplement composition comprising SGPs that can be combined with and/or incorporated into an animal feed and administered to (e.g., fed to) an animal to provide equivalent or superior effects on growth performance in the animal (e.g., compared to animals fed diets with other forms of supplemental selenium (e.g., selenium enriched yeast (e.g., SEL-PLEX)). In some embodiments, a dietary supplement composition of the invention increases the amount of circulating selenium (e.g., located in the blood and/or serum) in a subject (e.g. human or animal) receiving the composition. In some embodiments, a greater proportion of administered selenium is bioavailable in the soluble selenium compositions of the invention (e.g., SGPs) than in other selenuim formulations (e.g. sodium selenite or selenium enriched yeast (e.g. SEL-PLEX)). That is, in some embodiments, the invention provides compositions comprising selenoglycoproteins that contain a higher proportion and/or ratio of selenium that is made available (e.g., bioavailable) to a subject compared to other forms of selenium (e.g., selenium enriched yeast) meaning that lesser amounts of a composition comprising selenoglycoprotein of the invention are needed (e.g., to obtain similar bioavailability amounts). In some embodiments, a dietary supplement composition of the invention (e.g., comprising SGPs of the invention) increases the amount of selenium (e.g., located in muscle or, other tissue) in a subject (e.g. human or animal) receiving the composition. In some embodiments, SGPs and/or soluble selenium administration results in increased selenium bioavailability to serum, adipose tissue, muscle tissue, etc.

In some embodiments, the invention provides a method of increasing the efficiency by which an animal utilizes nutrients in a diet fed to the animal comprising providing to the animal a diet comprising a dietary supplement composition of the invention, wherein the supplement composition enhances the animal's ability to process and utilize the nutrients present in their diet. In some embodiments, a dietary supplement composition of the invention increases the amount of circulating antioxidants (e.g., selenium located in the blood and/or serum) in a subject receiving the composition. In some embodiments, a dietary supplement composition of the invention increases the amount of antioxidants (e.g., selenium located in adipose tissue, muscle, etc.) in a subject receiving the composition.

IV. Pharmaceuticals, Nutriceuticals, and Supplements

Nutritional selenium levels have been established by the FDA (See 21 C.F.R. 101.9(c)(8)(iv), January 1994). Humans and animals can safely metabolize limited amounts of both inorganic and organic forms of selenium and can convert non-methylated selenium to mono-ordi-or trimethylated derivatives, of which the monomethylated derivatives are most toxic. (See, e.g., Bedwal, R. S., et al., Medical Hypotheses, 41 (2):150-159 (August 1993)). The FDA has adopted Reference Daily Intakes (RDIs) of 70 micrograms for selenium for lactating women and RDI of 55 micrograms for non-lactating adults. Selenium dosage of 600 micrograms per day has been reported as safe. (See, e.g., Ferris G. M. Lloyd, et al., App. Clin. Biochem.,26:83-88 (1989). At about this dosage, normal activity of the enzyme glutathione reductase safely converts selengluthatione to hydrogen selenide in the liver and erythrocytes and is ultimately excreted. Thus, at such lower dosages, the body is able to safely metabolize and excrete selenium that is present in a free metallic form. However, as with many trace elements (e.g., selenium), at higher dosage levels or concentrations the beneficial effects are reversed and dangerous toxicity is manifested. (See, e.g., Furnsinn, C. et al., Internat'l J. of Obesity and Related Metab. Dis., 19(7):458-463 (1995)).

The administration of selenium in the natural form involves a scientific and medical trade-off because, when administered in relatively low concentrations, selenium provides beneficial health effects, however, at higher concentrations, selenium exhibits dramatic toxicity such that the potential health benefits are lost and toxicity becomes the primary concern.

As described above, the invention provides certain forms of selenium (e.g., SGPs, water-soluble selenium) that provide beneficial effects to a subject. Evidence has shown that organic forms of selenium (e.g., selenomethionine and selenium enriched yeast) may be less toxic and better absorbed than inorganic forms (See, e.g., Mahan, Proceedings of the 15th Annual Symposium Nottingham University Press, Nottingham, UK, pp. 523-535 (1999). Nonetheless, in some embodiments, multiple forms of selenium are used in combination with one another (e.g. to provide beneficial health effects to a subject). Natural sources of selenium include, but are not limited to, selenium enriched (e.g., selenized) yeast. The yeast strain used is not limiting.

In certain preferred embodiments of the invention, SGPs (e.g. derived from selenium enriched yeast (e.g. SEL-PLEX), as described in Examples 1-2) is the selenium form of choice for formulations and compositions of the invention. In some embodiments, compositions comprising water-soluble selenium and/or SGPs provide a more biologically available form of selenium compared to other forms of selenium. However, other forms of selenium may also find use in the invention including derivative or modifications of water-soluble selenium and/or SGPs, SEL-PLEX, or other forms of selenium enriched yeast, selenomethionine, selenocysteine, a selenite compound, a selenate compound, or derivatives, salts, or modifications thereof. Thus, in some preferred embodiments, each of these forms of selenium may be used as a component of a formulation. Alternatively, each of the above described forms of selenium may be linked (e.g., chemically or physically) to a drug or therapeutic to form a selenium-drug derivative. Additionally, compositions and formulations are not limited to one form of selenium. Indeed, a composition or formulation may comprise multiple forms of selenium (e.g., SGPs and SEL-PLEX, or Sod-sel and water-soluble selenium).

Other forms of selenium that find use in various embodiments of the present invention are described in U.S. Pat. Nos. 6,911,550 6,197,295, 5,221,545,6 and 6,576,233, and U.S. Pat. App. Nos. 20010043925, 20050069594, 20050089530, and 20080107755, herein incorporated by reference in their entireties.

Accordingly, the present invention provides pharmaceutical, nutriceutical, and/or supplement compositions that comprise one or more forms of selenium (e.g. SGPs, soluble selenium (e.g. water soluble selenium),etc.), alone or in combination with at least one other agent, such as a stabilizing compound, other therapeutic(s), nutrient(s), and or/minerals; and may be administered in any sterile, biocompatible carrier, including, but not limited to, saline, buffered saline, dextrose, water, etc.

The methods of the present invention find use in treating (e.g., prophylacticly or therapeutically) diseases or altering physiological states. Selenium (e.g., soluble selenium (e.g. water-soluble selenium), SGPs))) can be administered to a subject (e.g., a patient) intravenously in a pharmaceutically acceptable carrier such as physiological saline. Standard methods for intracellular delivery of compounds can be used (e.g., delivery via liposome). Such methods are well known to those of ordinary skill in the art. The formulations of this invention are useful for parenteral administration, such as intravenous, subcutaneous, intramuscular, and intraperitoneal.

As is well known in the medical arts, dosages for any one subject may depend upon many factors, including the patient's size, body surface area, age, the particular compound to be administered, sex, time and route of administration, general health, and interaction with other drugs being concurrently administered.

Accordingly, in some embodiments compositions and/or formulations comprising selenium (e.g., soluble selenium (e.g. water-soluble selenium), SGPs, etc.) can be administered to a subject alone, or in combination with other forms of selenium, drugs, small molecules, or in pharmaceutical compositions where it is mixed with excipient(s) or other pharmaceutically acceptable carriers. In some embodiments, the pharmaceutically acceptable carrier is pharmaceutically inert. In other embodiments, compositions comprising selenium (e.g., soluble selenium (e.g. water-soluble selenium), SGPs, etc.) are administered alone to individual subjects suffering from a disease or condition. In other embodiments of the present invention, compositions comprising selenium (e.g., soluble selenium (e.g. water-soluble selenium), SGPs, etc.) are administered alone to individual subjects for the promotion of general health or the health of a body system. Compositions comprising selenium (e.g., soluble selenium (e.g. water-soluble selenium), SGPs, etc.) alone or in combination with one or more other forms of selenium may be added to a nutritional drink or food (e.g., ENSURE, POWERBAR, or the like), a multi-vitamin, nutritional products, food products, etc. for daily consumption.

Depending on the target sought to be altered by treatment (e.g., gene expression associated with aging), these pharmaceutical, supplement, and/or nutriceutical compositions are formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration.

For injection, selenium-containing compositions (e.g. soluble selenium (e.g. water-soluble selenium), SGPs, etc.) are formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art.

In other embodiments, the selenium-containing compositions (e.g. soluble selenium (e.g. water-soluble selenium), SGPs, etc.) are formulated using pharmaceutically acceptable carriers well known in the art in dosages suitable for oral administration. Such carriers enable the selenium-containing compositions (e.g. soluble selenium (e.g. water-soluble selenium), SGPs, etc.) to be formulated as tablets, pills, capsules, liquids, gels, syrups, slurries, suspensions and the like, for oral or nasal ingestion by a patient to be treated.

Pharmaceutical compositions suitable for use in the present invention include compositions wherein the active ingredients (e.g., selenium-containing compositions (e.g. soluble selenium (e.g. water-soluble selenium), SGPs, etc.) are contained in an effective amount to achieve the intended purpose. For example, an effective amount of the pharmaceutical agent may be that amount that alters the expression of a specific gene (e.g., TGFB1, MAPK8, C1R, UBE4A, SMPX, USP22, and PTP4A1). Determination of effective amounts is well within the capability of those skilled in the art.

In addition to the active ingredients these selenium-containing (e.g. soluble selenium (e.g. water-soluble selenium), SGPs, etc.) pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

The pharmaceutical compositions of the present invention may be manufactured in a manner that is itself known (e.g., by means of conventional mixing, dissolving, granulating, dragee-making, levigating, emulsifying, encapsulating, entrapping or lyophilizing processes).

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethyl-cellulose; and gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, (i.e., dosage).

Pharmaceutical preparations which can be used orally include push-fit capsules made of gelatin, as well as soft, sealed capsules made of gelatin and a coating such as glycerol or sorbitol. The push-fit capsules can contain the active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Compositions comprising a compound of the invention formulated in a pharmaceutical acceptable carrier may be prepared, placed in an appropriate container, and labeled for treatment of an indicated condition. For compositions or formulations comprising selenium, conditions indicated on the label may include treatment of condition related to prophylactic or therapeutic treatment of neurodegenerative disease or cognitive function.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5 that is combined with buffer prior to use.

For any compound used in the methods of the invention, the therapeutically effective dose can be estimated initially from cell culture assays. Then, preferably, dosage can be formulated in animal models (particularly murine models) to achieve a desirable circulating concentration range.

A therapeutically effective dose refers to that amount of which ameliorates or prevents symptoms of a disease state or condition (e.g., through altering gene expression) Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds which exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The exact dosage may be chosen by a subject or by a physician in view of the patient to be treated. Dosage and administration are adjusted to provide sufficient levels of the active moiety or to maintain the desired effect (e.g., alteration of gene expression in a subject). Additional factors that may be taken into account include the severity of the disease state; age, weight, and gender of the patient; diet, time and frequency of administration, drug combination(s), reaction sensitivities, and tolerance/response to therapy. Long acting pharmaceutical compositions might be administered every 3 to 4 days, every week, or once every two weeks or once every month depending on half-life and clearance rate of the particular formulation.

In some embodiments, selenium (e.g., soluble selenium, water-soluble selenium, SGPs, etc.) is administered at a daily dose of between 25 and 600 μg per day (e.g., soluble selenium, water-soluble selenium, and/or SGP is administered to a subject in such a way so as to provide between 25 and 600 μg of selenium to the subject each day). In preferred embodiments, the selenium is administered at a daily dose of between 50 and 200 μg per day. In other preferred embodiments, selenium is administered at a daily dose of between 100 and 200 μg per day. Doses outside of 25 and 600 μg may be used. In some embodiments, a single dose of selenium (e.g., soluble selenium, water-soluble selenium, SGPs, etc.) is administered once daily. In other embodiments, 2, 3, 4, or more doses may be administered each day (e.g., once in the morning and once at night, or once every 4 to 6 hours). For example, in some embodiments, selenium (e.g., soluble selenium, water-soluble selenium, SGPs, etc.) is administered to a subject in three separate, more than three separate, two separate, or less than two separate doses. In some preferred embodiments, the daily dose is administered in a time release capsule. In some preferred embodiments, the daily dose is between 25-75 μg of selenium (e.g., soluble selenium, water-soluble selenium, SGPs, etc.). In other preferred embodiments, the daily dose is 200 μg of selenium (e.g., organic selenium, selenized yeast, SEL-PLEX, soluble selenium, water-soluble selenium, SGPs, etc.).

The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Compositions and formulations comprising selenium are believed to be particularly useful for oral administration.

Selenium-containing (e.g. SGP-containing) pharmaceutical, nutriceutical, and/or supplement compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Thus, in some embodiments, pharmaceutical, nutriceutical, and/or supplement compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical, nutriceutical, and/or supplement formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

In some embodiments, the selenium-containing (e.g. soluble selenium, water-soluble selenium, SGP) compositions of the present invention may be formulated into any of many possible dosage forms such as, but not limited to, tablets, capsules, liquid syrups, soft gels, suppositories, and enemas. The compositions of the present invention may also be formulated as time-release nanoparticles (e.g. nanocapsules), vesicles, liposomes, polymers (e.g. molecularly imprinted polymers (MIPs), biodegradable slow-release polymers, polycationic polymers, etc. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers. In one embodiment of the present invention the pharmaceutical, and/or supplement compositions may be formulated and used as foams. Foams include formulations such as, but not limited to, emulsions, microemulsions, creams, jellies and liposomes. While basically similar in nature these formulations vary in the components and the consistency of the final product.

The selenium-containing (e.g. soluble selenium, water-soluble selenium, SGP, etc.) compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

In some embodiments, the invention provides pharmaceutical, nutriceutical, and/or supplement compositions containing (a) one or more forms of selenium (e.g., SGP, soluble selenium, water-soluble selenium, SEL-PLEX) and (b) one or more other agents (e.g., nutrient, mineral, therapeutic, etc.).

The present invention also includes methods involving co-administration of compounds comprising selenium (e.g. soluble selenium, water-soluble selenium, SGP, etc.) described herein with one or more additional active agents (e.g., a therapeutic, anti-oxidant, etc.). Indeed, it is a further aspect of this invention to provide methods for enhancing therapies and/or pharmaceutical. nutriceutical, and/or supplement compositions by co-administering a composition comprising selenium (e.g. soluble selenium, water-soluble selenium, SGP, etc.) of this invention. In co-administration procedures, the agents may be administered concurrently or sequentially. In one embodiment, the compounds described herein are administered prior to the other active agent(s). The formulations and modes of administration may be any of those described above. In addition, the two or more co-administered agents may each be administered using different modes or different formulations.

V. Antioxidants

In some embodiments of the present invention, antioxidants are co-administered with compositions or formulations of the present invention. The present invention is not limited by the type of antioxidant utilized. Indeed, a variety of antioxidants are contemplated to be useful in the present invention including, but not limited to, alkylated diphenylamines, N-alkylated phenylenediamines, phenyl-.alpha.-naphthylamine, alkylated phenyl-.alpha.-naphthylamine, dimethyl quinolines, trimethyldihydroquinolines and oligomeric compositions derived therefrom, hindered phenolics, alkylated hydroquinones, hydroxylated thiodiphenyl ethers, alkylidenebisphenols, thiopropionates, metallic dithiocarbamates, 1,3,4-dimercaptothiadiazole and derivatives, oil soluble copper compounds, and the like, Naugalube® 438, Naugalube 438L, Naugalube 640, Naugalube 635, Naugalube 680, Naugalube AMS, Naugalube APAN, Naugard PANA, Naugalube TMQ, Naugalube 531, Naugalube 431, Naugard BHT, Naugalube 403, and Naugalube 420, ascorbic acid, tocopherols including alpha-tocopherol, water-soluble antioxidants such as sulfhydryl compounds and their derivatives (e.g., sodium metabisulfite and N-acetyl-cysteine), lipoic acid and dihydrolipoic acid, resveratrol, lactoferrin, ascorbic acid derivatives (e.g., ascorbyl palmitate and ascorbyl polypeptide), butylated hydroxytoluene, retinoids (e.g., retinol and retinyl palmitate), tocotrienols, ubiquinone, extracts containing flavonoids and isoflavonoids and their derivatives (e.g., genistein and diadzein), extracts containing resveratrol and the like, grape seed, green tea, pine bark, propolis, Irganox1010, 1035, 1076, 1222 (manufactured by Ciba Specialty Chemicals Co., Ltd.), Antigene P, 3C, FR, Sumilizer GA-80 (manufactured by Sumitomo Chemical Industries Co., Ltd.), beta-carotene, lycopene, vitamins C, E, and A, and other substances.

Although an understanding of the mechanism is not necessary to practice the present invention and the present invention is not limited to any particular mechanism of action, in some embodiments, administering a selenium-containing composition (e.g. soluble selenium, SGP) to a subject changes gene expression profiles (e.g., TGFB1, MAPK8, C1R, UBE4A, SMPX, USP22, and PTP4A1) in the subject. In some embodiments, administering a selenium-containing composition (e.g. soluble selenium, SGP) to a subject reduces the level of DNA damage (e.g. in brain tissue (e.g., neocortex), muscle tissue, adipose tissue, etc.) of a subject.

In some embodiments, the present invention provides a method of reducing sensitivity of cells to $H_2O_2$ cytotoxicity comprising administering to the cells a selenium-containing composition (e.g. soluble selenium, water-soluble selenium, SGP, SEL-PLEX, etc.).

The invention further provides a method of reducing superoxide radicals in a subject (e.g., in a subject experiencing oxidative stress) comprising administering a composition (e.g., a nutritional supplement) comprising selenium (e.g. soluble selenium, water-soluble selenium, SGP, SEL-PLEX, etc.) to the subject. Furthermore, in some embodiments, the present invention provides that subjects receiving certain compositions comprising selenium (e.g. soluble selenium, water-soluble selenium, SGP, SEL-PLEX, etc.) have an enhanced ability to deal with oxidative stress. Although an understanding of the mechanism is not necessary to practice the present invention and the present invention is not limited to any particular mechanism of action, in some embodiments, subjects receiving a composition comprising selenium (e.g., a dietary supplement comprising selenium (e.g. soluble selenium, water-soluble selenium, SGP, SEL-PLEX, etc.)) have an enhanced ability to cope with oxidative stress due to the ability of select forms of selenium (e.g. soluble selenium, water-soluble selenium, SGP, SEL-PLEX, etc.) to alter (e.g., reduce) the level of superoxide radicals in the subject.

It is contemplated that the compositions and methods of the present invention will find use in various settings, including, but not limited to, research and clinical diagnostics.

VI. Carriers

In some embodiments, the present invention provides delivery of selenium (e.g. selenoglycoprotein) via one or more carriers including, but not limited to nanoparticles (e.g. nanocapsules), vesicles, liposomes, polymers (e.g. molecularly imprinted polymers (MIPs), slow-release polymers, polycationic polymers, and/or polymerosomes. In some embodiments, a selenium carrier provides administration, targeting, and/or timed release of selenium-containing compounds (e.g. water-soluble selenium, SGP) in a subject (e.g. human or animal). In some embodiments, carriers (e.g. slow-release polymer, nanocapsule, MIP, polymerosomes, etc.) enhance delivery of selenium-containing compounds (e.g. organic selenium, soluble selenium, water-soluble selenium, SGP, SEL-PLEX, etc.) to a subject. In some embodiments, carriers (e.g. slow-release polymer, nanocapsule, MIP, polymerosomes, etc.) increase the bioavailability of selenium-containing compounds (e.g. organic selenium, soluble selenium, water-soluble selenium, SGP, SEL-PLEX, etc.) to a subject.

The invention is not limited by the type of carrier utilized. Indeed a variety of carriers may be used including, but not limited to, dendrimers, polymerosomes, nanoparticles, slow-release polymers, nanocapsules, molecularly imprinted polymers and/or other type of carrier. In one preferred embodiment, the carrier is a slow-release polymer. In another preferred embodiment, the carrier is a molecularly imprinted polymer. In still another preferred embodiment, the carrier is a polymersome used to encapsulate selenoglycoprotein. The invention is not limited by the type of polymersome used. Indeed, any polymersome known in the art may be utilized. In some embodiments, the polymersome comprises poly(ethylene oxide) (PEO) block copolymer. However, the invention is not so limited. Any known block copolymer may be utilized, including, for example poly(ethylethylene) (PEE), poly(butadiene) (PB or PBD), poly(styrene) (PS), and poly(isoprene) (PI). In some embodiments, the polymer comprises poly($\epsilon$-caprolactone) (PCL) diblock co-polymer. In some embodiments, the polymersome comprises poly(ethylene oxide)-block-poly($\epsilon$-caprolactone) (PEO-b-PCL) based diblock copolymers. In some embodiments, the polymersome comprises a block copolymer that is a triblock, tetrablock, pentablock, or at least six block copolymer. In some embodiments, the polymersome is derived from the coupling of poly(lactic acid), poly(glycolide), poly(lactic-coglycolic acid) and/or or poly(3-hydroxybutyrate) with PEO. The invention is not limited by the size of a polymersome encapsulated selenoglycoprotein. A variety of sizes find use in the compositions and methods of the invention including, but not limited to, polymersome encapsulated selenoglycoproteins that are about, 50-300 nm in diameter although larger (e.g., about 350 nm, 400 nm, 500 nm or larger) and smaller (e.g., about 40 nm, 30 nm, 20 nm, or smaller) polymersome encapsulated selenoglycoproteins may be used.

In some embodiments, the present invention comprises SGP controlled-release nanocapsules and MIP spheres to provide steady and safe supply of organic selenium (e.g. molecularly imprinted polymers (MIPs), slow-release polymers, etc.) in comparison with other forms of selenium (e.g. selenium enriched yeast, SEL-PLEX, or inorganic selenium single doses capsules or pills). In some embodiments, water-soluble, soluble, and/or SGPs are utilized for efficient encapsulation and delivery of selenium through the advanced delivery methods herein (e.g. nanoparticles (e.g. nanocapsules), vesicles, polymers (e.g. molecularly imprinted polymers (MIPs), slow-release polymers, etc.), and/or polymerosomes). In some embodiment, the advanced delivery methods herein enhance the bioavailability of the encapsulated selenium (e.g. SGPs or soluble selenium). In some embodiments, the advanced delivery methods herein provide slow-release (e.g. 12 hours, 24 hours, 2 days, 1 week, 2 weeks, 3 weeks, 10 weeks, etc.) of selenium into a solution, a subject, serum, etc.

In some embodiments, the invention provides slow-release polymers as a carrier for selenium-containing compositions (e.g. organic selenium, soluble selenium, water-soluble selenium, SGP, etc.) of the present invention. Slow release polymers, such as poly(lactic acid-co-glycolic acid) (PLGA), or polycationic polymers, such as, polyethyleneimine (PEI), may be utilized as carriers. In some embodiments, slow-release polymers provide controlled delivery of selenium containing compositions (e.g. organic selenium, soluble selenium, water-soluble selenium, SGP, SEL-PLEX, etc.). In some embodiments, controlled delivery occurs when a polymer (e.g. PEI), whether natural or synthetic, is judiciously combined with a selenium-containing composition (e.g. organic selenium, soluble selenium, water-soluble selenium, SGP, SEL-PLEX, etc.) and optionally other active or inactive agents in such a way that the selenium-containing composition (e.g. organic selenium, soluble selenium, water-soluble selenium, SGP, SEL-PLEX, etc.) is released from the material in a predesigned manner. The release of the selenium-containing composition (e.g. organic selenium, soluble selenium, water-soluble selenium, SGP, SEL-PLEX, etc.) may be constant over a long period, it may be cyclic over a long period, or it may be triggered by the environment or other external events. In some embodiments, controlling delivery provides more effective therapy. In some embodiments, controlling delivery eliminates the potential for both under- and overdosing. Other advantages of using controlled-delivery systems can include the maintenance of selenium levels within a desired range, the need for fewer administrations, and increased patient compliance.

In some embodiments, the invention provides polymerosomes as carriers for selenium-containing compositions (e.g. organic selenium, soluble selenium, water-soluble selenium, SGP, SEL-PLEX, etc.) of the present invention. In some embodiments, polymersomes are made using amphiphilic synthetic block copolymers to form the vesicle membrane, and have radii ranging from about 50 nm to about 10 um or more (See, e.g., Discher et al. Journal of Physical Chemistry B (2002), 106(11), 2848-2854), herein incorporated by reference in its entirety). In some embodiments, polymersomes contain an aqueous solution in their core and are useful for encapsulating and protecting molecules, such as selenium-containing compositions (e.g. organic selenium, soluble selenium, water-soluble selenium, SGP, SEL-PLEX, etc.) and optionally one or more of drugs, enzymes, other proteins and peptides, and DNA and RNA fragments. In some embodiments, the polymersome membrane provides a physical barrier that isolates the encapsulated material from external materials, such as those found in biological systems. In some embodiments, polymerosomes allow timed release of contents within their core (e.g. selenium-containing compositions (e.g. organic selenium, soluble selenium, water-soluble selenium, SGP, SEL-PLEX, etc.)). In some embodiments, the use of synthetic polymers to construct polymerosomes enables designers to manipulate the characteristics of the membrane and thus control permeability, release rates, stability and other properties.

In one embodiment, the selenium-containing (e.g. soluble selenium, water-soluble selenium, SGP) compositions of the present invention may be encapsulated inside poly(ethylene oxide)-block-poly(ε-caprolactone) (PEO-b-PCL) based polymersomes. Although an understanding of a mechanism is not necessary to practice the invention, and the invention is not limited to any particular mechanism of action, in some embodiments, PEO provides the resultant carrier improved in vitro chemical and mechanical stability, augmented in vivo bioavailability and prolonged blood circulation half-lives. PCL, a well-known implantable biomaterial, forms the polymersome membrane, and facilitates complete and safe in vivo degradation of resulting product by hydrolysis of its ester linkages.

In another embodiment, the selenium-containing compositions (e.g., selenoglycoproteins) of the present invention may be encapsulated in polymersomes synthesized from blends or pure derivatives of other biodegradable block polymers derived from the coupling of poly(lactic acid), poly (glycolide), poly(lactic-coglycolic acid) or poly(3-hydroxybutyrate) with PEO.

In some embodiments, the present invention provides nanocapsules (Couvreur et al. Crit Rev Ther Drug Carrier Syst. 2002; 19(2):99-134, herein incorporated by reference in its entirety) as carriers for selenium-containing compositions (e.g. organic selenium, soluble selenium, water-soluble selenium, SGP, SEL-PLEX, etc.) of the present invention (See, e.g., U.S. Pat. No. 7,498,045, herein incorporated by reference in its entirety). In some embodiments, nanocapsules provide controlled release of selenium-containing compositions (e.g. organic selenium, soluble selenium, water-soluble selenium, SGP, SEL-PLEX, etc.) upon biodegradation of the nanocapsule. In some embodiments, nanocapsules have biodegradation half-lives of about 2 to about 100 hours (e.g. about 2 hours . . . 4 hours . . . 6 hours . . . 12 hours . . . 24 hours . . . 48 hours . . . 96 hours, etc.). In some embodiments, biodegradable nanocapsules of the invention are adaptable for the controlled release of selenium-containing compositions (e.g. organic selenium, soluble selenium, water-soluble selenium, SGP, SEL-PLEX, etc.) and optionally a variety of other encapsulated therapeutic agents, including macromolecules, into in vivo circulation of a subject upon administration thereto. The nanocapsule compositions of the present invention are further adapted to encapsulate therapeutically effective concentrations of selenium-containing compositions (e.g. organic selenium, soluble selenium, water-soluble selenium, SGP, etc.) and deliver the same into in vivo circulation of a recipient. In some embodiments, a nanocapsule encapsulates selenium-containing compositions (e.g. organic selenium, soluble selenium, water-soluble selenium, SGP, SEL-PLEX, etc.) is a membrane comprising, for example, a copolymer of polylactic acid polymer and polyethylene glycol. In some embodiments, nanocapsules are formed by the interfacial polymerization of a monomer or the interfacial nanodeposition of a preformed polymer.

In some embodiments, the present invention provides molecularly imprinted polymers as carriers for selenium-containing compositions (e.g. organic selenium, soluble selenium, water-soluble selenium, SGP, SEL-PLEX, etc.) of the present invention (Mosbach. Trends in Biochemical Sciences, Vol. 7, pp. 92-96, 1994, Wulff. Trends in Biotechnology, Vol. 11, pp. 85-87, 1993, Andersson, et al., Molecular Interactions in Bioseparations (Ngo. T. T. ed.), pp. 383-394,), U.S. Pat. No. 5,959,050, herein incorporated by reference in their entireties Experimental The following examples are provided in order to demonstrate and further illustrate certain preferred embodiments and aspects of the present invention and are not to be construed as limiting the scope thereof.

EXAMPLE 1

Soluble SGP Separation and Testing

Dilute hydrochloric acid extraction of selenoproteins from SEL-PLEX was carried out at pH 1.5 for 8 hrs and at 80° C. The acidic extract (pH 1.5) was separated from the insoluble residue by centrifugation. SGP's were precipitated from the extract by incremental adjustment of the extract pH to: 1.85, 3.0, 4.0, and 6.0 using 2N sodium hydroxide (e.g., as more fully described in Example 2). The precipitated SGP's were separated from the solution by centrifugation and the pellets were washed three times with deionized water and freeze dried. Using precipitation instead of salting off or concentrating large volumes conserved reagents and labor (and costs associated therewith) and decreased the environmental impact of the method. The pellet containing solid residues from the first extraction was washed with the liquids of pH 1.85 from the second extraction to reduce the volume of water used in the process, and to dissolve most of the SGP's trapped within the pellet from the first centrifugation. The solid residues from the second centrifugation which contain significant amount of selenium can be blended with a fresh batch of selenium yeast before it is spray-dried, and therefore result with a complete utilization of the material that was taken for the extraction. The extracted fractions of SGP's constituted from 2.0 to 2.5 weight % of SEL-PLEX and from 4.3 to 5.75% of total selenium that was present in pre-extraction SEL-PLEX.

Fractions precipitated at pH 1.85 yielded the highest content of selenium and the lowest content of protein. The higher value of the pH during the pH dependent SGP's precipitation, the higher content of the protein and lower content of the carbohydrate component in the SGP fraction. Fractions that were precipitated at pH 6.0 had the highest protein (~95 weight %) and the lowest content of the carbohydrate component (fiber). The content of protein for the set of fractions from acidic extraction ranged from 60 to 96 weight %, and the level of selenium for the same set of fractions was between 3800 ppm and 2600 ppm range. These SGP fractions contained from 4 to 37 weight % of carbohydrate component.

Gel electrophoresis of the original mixture of SGP's from SEL-PLEX extraction revealed that bands corresponding to high molecular weight proteins or proteins carrying a large carbohydrate component were absent. Similar size distribution, with domination of low molecular weight fractions, was detected using capillary electrophoresis and the low molecular weight proteins from 5.1 kDa to 12.2 kDa comprised more than 90% of the mixtures.

Size exclusion chromatography of SGP fractions on Bio-Rad P10 gel (retention times up to 6 hrs) and on Bio-Rad P30 gel (less than one hour retention time), resulted in an early peak with the retention time 5-10 minutes and a broad, later peak, with the retention time 35-60 minutes. The early peak contained significantly more protein: from 64.74 to 75.24%, and significantly higher selenium concentration: from 2972 to 4252 ppm. The content of protein in the late peak was much lower: from 31.66 to 54.95% and the selenium concentration was significantly lower: from 1193 to1858 ppm. This type of chromatography can produce SGP's with high content of Se from crude fractions, and demonstrated low homogeneity of the carbohydrate component in these mixtures.

Size exclusion chromatography on Superdex Peptide 10/300 GL resin (Amersham Biosciences; fractionation range 7.0-100 kDa) using 0.1M AcONH$_4$ (pH 7.5) of various peptides from tryptic digestion, have produced similar set of peaks for SGP samples (10-100 kDa and >100 kDa) and completely different elution pattern for the SEL-PLEX sample. Only the "early" peaks, with the elution time below 20 min, contained selenium. The selenium containing eluents were collected, lyophilized and analyzed using SEC ICP MS, MALDI TOF MS and nano ESI MS/MS techniques. The results were complementary and allowed the detection, identification and sequencing of selenium containing peptides. The proteins identity was obtained by SwissProt data base search (SEE Table 1).

and 6.0, were spiked into chicken feed. Each of the samples contained 7.5 mg of selenium that was needed to obtain 25 kg feed that contained 0.3 ppm selenium. It was found that the sample of the pH 4.0 delivered the same quantity of selenium as SEL-PLEX in spite of 43% lower weight. Although an understanding of a mechanism is not needed to practice the invention, and the invention is not limited to any particular mechanism of action, in some embodiments, the pH 4.0 dependent fraction of selenoglycoproteins delivered the same quantity of selenium due to higher selenium concentrations in the pH 4.0 dependent fraction of selenoglycoproteins compared to SEL-PLEX. Similar quantity of selenium was also delivered by the sample of pH 6.0. Thus, the invention provides that SGP's separated from SEL-PLEX and precipitated from the extract (e.g., at a pH from 4.0 to 6.0) are useful for delivery of selenium to tissue of a subject (e.g., chicken muscles) by oral administration. The efficiency of selenium delivery was roughly directly proportional to the protein content in the fractions and the content of selenomethionine and not to the total concentration of selenium. Therefore, pH dependent fractions of selenium enriched yeast extract precipitated at a pH between 4.0 and 6.0 can be used to deliver

TABLE 1

Identified seleno-peptides and selenoproteins from SEL-PLEX extract.

| SEC fraction analyzed | Detected peptide mass ($^{80}$Se) [M + H]$^+$, Th | Identified peptide sequence | Protein | Protein molecular mass (kDa) |
|---|---|---|---|---|
| 2 | 653.39 | GSDTMRSVSPIR SEQ ID NO: 1 | Ylr 190 wp | 42 |
|   | 701.42 | GSDTSeMRSVSPIR SEQ ID NO: 2 |  |  |
| 3 | 637.39 | SGMSKK SEQ ID NO: 3 | Phosphatidylinositol 4 kinase alpha | 89 |
|   | 685.41 | SGSeMSKK SEQ ID NO: 4 |  |  |
| 2 | 587.33 | EVIGIDPSSAMLSIAEK SEQ ID NO: 5 | Yhr209wp | 34 |
|   | 635.35 | EVIGIDPSSASeMLSIAEK SEQ ID NO: 6 |  |  |
| 3 | 637.39 | ASeMIVR SEQ ID NO: 7 | Ribonuclease III | 77 |
| 1 and 2 | 402.10 | DYSeMGAAK SEQ ID NO: 8 | HSP 12 | 12 |
| 1 and 2 | 489.55 | SIVPLSeMDR SEQ ID NO: 9 | HSP 10 | 10 |
| 1 and 2 | 504.03 | SeMGHDQSGTK SEQ ID NO: 10 | SIP 18 | 18 |

Detection of the same type seleno-proteins in two different fractions from the acidic extraction of SEL-PLEX indicated that the extraction process involved hydrolysis of the carbohydrate part of these SGP's rather than cleavage of the bond between the carbohydrate and the protein part of the SGP molecule. Development of a practical method for extraction and fractionation of soluble SGP's from SEL-PLEX allowed generation of enough material to run animal feeding studies in which efficiency of Se delivery to chicken muscle by sodium selenite, SEL-PLEX and four fractions of soluble SGP's were compared (See, e.g., Examples 3 and 4).

A sample of SEL-PLEX and four samples of SGP's prepared by pH dependent precipitation of the acidic extract from the same sample of SEL-PLEX at the pH 1.85, 3.0, 4.0 organic selenium to a subject by oral route. The delivery of inorganic selenium was around ten times lower in comparison with these fractions of SGP's.

EXAMPLE 2

Soluble SGP Separation

Acidic extraction of SEL-PLEX (See, e.g., FIG. 2). A 4 L three neck reactor (e.g. extractor #1, See, e.g., FIG. 2) equipped with a mechanical stirrer, thermometer, and an electric blanket was charged with 3 L of deionized H$_2$O and 50 ml of 12.1 M HCl while stirring. The reactor was heated to above 50° C. and 600 g of SEL-PLEX were added in portions with stirring. After approximately an hour when the temperature reached 80° C. the pH of the mixture was 2.23. This was adjusted to 1.5 by the addition of 13.5 mL of 12.1 M HCl. The reaction vessel was maintained with heating and stirring for 7 hrs. The pH of the mixture was checked approximately every hour to ensure it was maintained at 1.5. The acidic post-reaction mixture (pH 1.5) was charged into four 1 L centrifuge jars and centrifuged (centrifuge #1, See FIG. 2) at 4000 RCF for 20 min at 8° C. A clear supernatant (pH 1.5) and the solids were collected. The supernatant was charged into a 3 L 3-neck reactor (mixer #1, See FIG. 2), placed in an ice-water bath, and equipped in a dropping funnel containing 2N NaOH, a mechanical stirrer and a pH electrode. The stirrer was started and 2N NaOH was added drop-by-drop to the solution, until the pH meter indicated an increase of the pH of the mixture to 1.85. During NaOH addition a white precipitate was formed. Stirring was continued for 30 min and the mixture was centrifuged again (centrifuge #2, See FIG. 2) and the pellet from SGP's precipitation at the pH 1.85 was collected and freeze-dried (freeze-drier #1, See FIG. 2) to yield 1.635 g of white precipitate. The supernatant from the second centrifugation (pH 1.85) was mixed (mixer #2, See FIG. 2) with the pellet (pH 1.5) from the first centrifugation for 30 min at the temperature of ice-water bath (4° C.) and centrifuged (centrifuge #3, See FIG. 2) to yield the wet residue solids and a supernatant of pH 1.6 from which the pH 3.0, 4.0 and 6.0 SGP fraction were separated by pH dependent precipitation.

Figure 3:
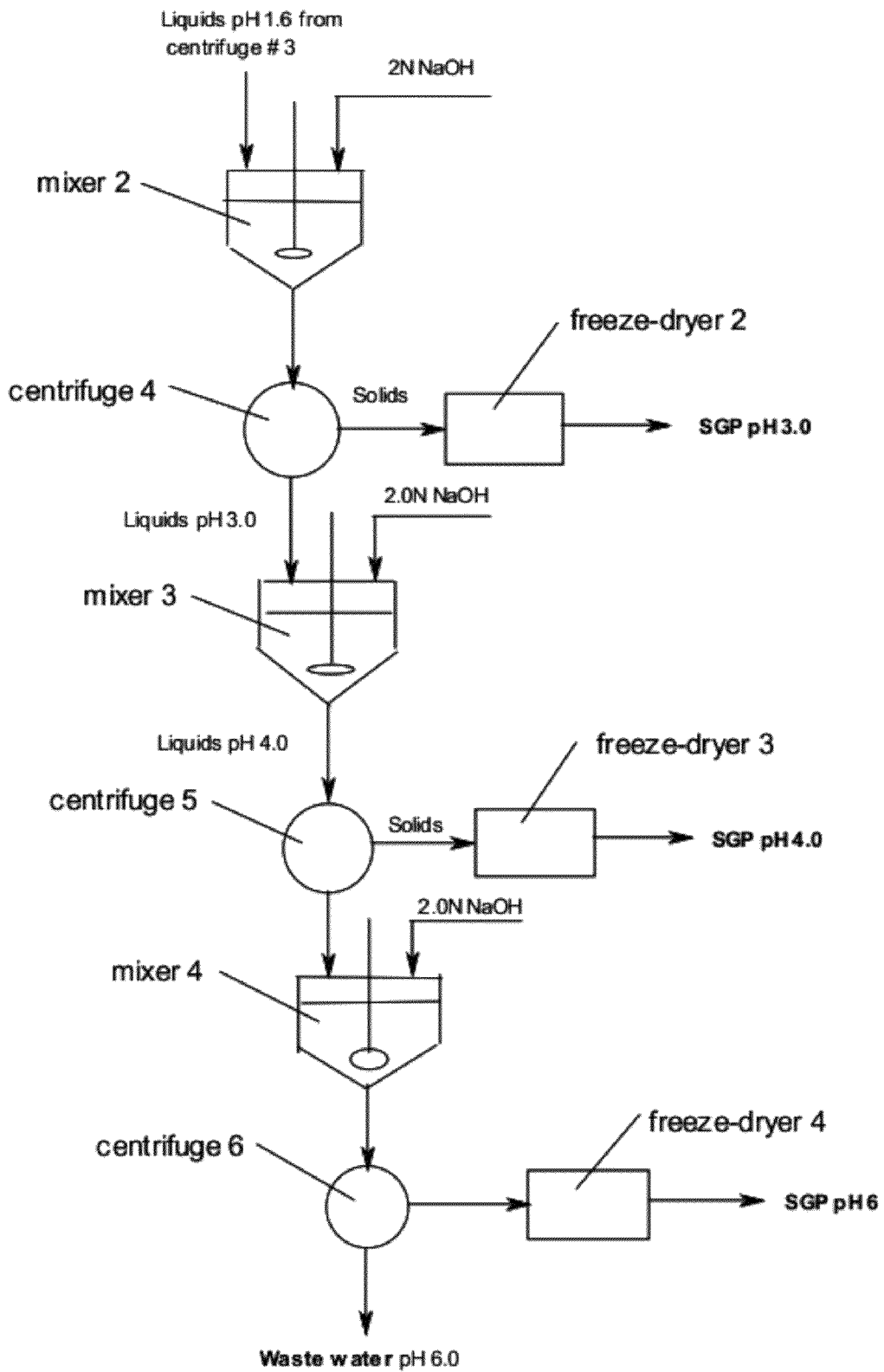
FIG. 3 shows a schematic of an embodiment of the present invention.

A pH dependent precipitation of SGP's (See FIG. 3). The supernatant of the pH 1.6 was charged into a mixer #3 (See FIG. 3) and the pH of the solution adjusted to 3.0 by the addition of 2N NaOH. The stirring was maintained for 30 more minutes and the precipitate of SGP pH 3.0 that formed was collected by centrifugation (centrifuge #4, See FIG. 3) and freeze-dried yielding a light grey precipitate. The supernatant of the pH 3.0 was charged into a mixer #4 (See FIG. 3) and the pH of the solution was adjusted to 4.0 by the addition of 2N NaOH. The stirring was maintained for 30 more minutes and the precipitate of SGP pH 4.0 that formed, was collected by centrifugation (centrifuge #5, See FIG. 3) and freeze-dried yielding the light grey precipitate. The supernatant of the pH 4.0 was charged into a mixer #5 (See FIG. 3) and the pH of the solution adjusted to 6.0 by the addition of 2N NaOH. The stirring was maintained for 30 more minutes and the precipitate of SGP pH 6.0 that formed was collected by centrifugation (centrifuge #6, See FIG. 3) and freeze-dried yielding the light grey precipitate. Subsequent precipitates that had formed were collected by centrifugation. Waste water stream of pH 6.0 from the last centrifugation which contained some seleno-peptides, mannose and glucose oligosaccharides, can be utilized in preparation of yeast growth media. Therefore, the process did not produce toxic waste and is environmentally friendly.

TABLE 2

The averaged results from three subsequent extractions of 600 g of SEL-PLEX.

| Fraction pH | Se concentration [ppm] | Protein weight [%] | Weight [G] |
|---|---|---|---|
| 1.85 | 4887 | 65.55 | 1.635 |
| 3.0 | 3836 | 76.04 | 5.652 |
| 4.0 | 3250 | 87.74 | 3.634 |
| 6.0 | 2915 | 91.81 | 1.757 |

EXAMPLE 3

Bioavailability Comparison

Chicks were fed for eighteen days with seven different dietary treatments (See Tables 3 and 4) to compare the bioavailability of selenium from the pH dependent precipitation of SGP's from SEL-PLEX acidic extract by measuring selenium content in chicken breast muscle:

TABLE 3

Composition and nutrient specification of basal diet

| Ingredient | % |
|---|---|
| Corn | 57.80 |
| Soybean meal (48%) | 35.00 |
| Corn oil | 3.20 |
| Limestone | 1.30 |
| Dicalcium phosphate | 1.80 |
| Salt | 0.45 |
| Vit-Min Mix (no Se) | 0.25 |
| DL-Methionine | 0.20 |
| Total | 100 |
| Nutrient | |
| ME, kcal/kg | 300 |
| CP, % | 21.5 |
| Ca, % | 1.00 |
| Available P, % | 0.45 |
| Lysine, % | 1.21 |
| Methionine, % | 0.54 |
| Met + Cys, % | 0.89 |
| Na, % | 0.20 |

TABLE 4

Dietary treatments

| Treatment | Ingredients |
|---|---|
| 1 | Corn-soy basal diet with no Se supplementation |
| 2 | Basal + 0.3 ppm Se as sodium selenite |
| 3 | Basal + 0.3 ppm Se as SEL-PLEX |
| 4 | Basal + 0.3 ppm Se as fraction precipitated at pH 1.85 |
| 5 | Basal + 0.3 ppm Se as fraction precipitated at pH 3.0 |
| 6 | Basal + 0.3 ppm Se as fraction precipitated at pH 4.0 |
| 7 | Basal + 0.3 ppm Se as fraction precipitated at pH 6.0 |

As shown in Table 5, chickens fed with feed spiked (as shown in Table 4) with SGP fractions of: pH 4.0 and 6.0 accumulated almost the same quantity of selenium as chicken fed with SEL-PLEX. The levels of selenium that deposited in chicken breast muscle were above five times higher than in chicken fed with feed spiked with sodium selenite. The selenium concentration in: the SEL-PLEX spike was 1600 ppm, in the fraction pH 4.0 was equal to 3250 ppm and in the fraction pH 6.0 was equal to 2915 ppm, therefore smaller samples of SGP's were used for spiking.

TABLE 5

Effects of dietary Se sources on muscle Se concentration

| Treatment | Se, ppm |
|---|---|
| 1 - Basal | 98.9$^e$ |
| 2 - SodSel | 137.3$^d$ |
| 3 - SEL-PLEX | 327.6$^a$ |

TABLE 5-continued

Effects of dietary Se sources on muscle Se concentration

| Treatment | Se, ppm |
|---|---|
| 4 - pH 1.8 | 214.8$^c$ |
| 5 - pH 3.0 | 257.7$^b$ |
| 6 - pH 4.0 | 326.6$^a$ |
| 7 - pH 6.0 | 305.4$^a$ |

EXAMPLE 4

In vivo Effects of Different Selenium Treatments

Breast muscle from chickens referenced in Example 3 was used to assess similarities and differences in gene expression profiles elucidated by the following dietary treatments: Treatment 1-basal (no selenium added); Treatment 2-0.3 ppm sodium-selenite; Treatment 3-0.3 ppm SEL-PLEX; Treatment 6-0.3 ppm selenoglycoprotein (SGP) extracted from SEL-PLEX at pH 4.0 as described in Example 2. Treatment 6 was analyzed because it resulted in almost identical levels of selenium-deposition in breast tissue as was obtained with treatment with SEL-PLEX (See Table 5). As such, experiments were conducted during development of embodiments of the invention in order to determine if animals receiving Treatment 6 resulted in the same in vivo effects (e.g., gene expression changes) observed in the SEL-PLEX fed animals, or whether significant differences existed that could be measured.

Animals and Tissue Sampling:

At 18-days of age, five chickens from each treatment group (described above and in Tables 3 and 4) were randomly selected and euthanized by argon asphyxiation, followed by cervical dislocation. Samples of breast muscle (1 gram) were rapidly removed and flash frozen in liquid nitrogen. Samples were stored at −80° C. until analyzed.

Microarray Analysis:

Total RNA was isolated from frozen tissue using TRIZOL reagent (INVITROGEN, Carlsbad, Calif.) according to the manufacturer's protocol and purified using a RNEASY kit (QIAGEN, Valencia, Calif.). Total RNA was quantified by absorbance at 260 nm and integrity was confirmed by agarose gel electrophoresis and ethidium bromide staining of the 28S and 18S bands.

Microarray profiling was performed using the AFFYMETRIX (Santa Clara, Calif.) Chicken Genome Array following the manufacturer's suggested protocols. Individual samples were prepared and hybridized to the array.

Data were processed and each probe set was labeled as P (present), M (marginal) or A (absent) based the ratio of signal to noise strength using the AFFYMETRIX MAS5.0 expression summary.

Bioinformatics Analysis

GeneSpring GX 10.0 (Silicon Genetics, Redwood, Calif.) was used to qualify and normalize microarray data and to perform statistical and gene expression pattern analyses. The percent of genes expressed on the Chicken Genome Array was calculated using the number of probe sets labeled P or M based on an applied algorithm.

To minimize the possibility of misleading findings, probe sets with very low signal intensity (labeled as 'Absent' by the AFFYMETRIX algorithm) were excluded from further analysis. After data were uploaded to GeneSpring, a t-test was used to identify differentially-expressed transcripts. Only genes that differed from the control group receiving treatment 1 ($P \leq 0.05$) and that had a corresponding signal intensity fold change (FC)$\geq$1.2 relative to the control were deemed changed. Genes not meeting these criteria were excluded from analysis.

Figure 4:
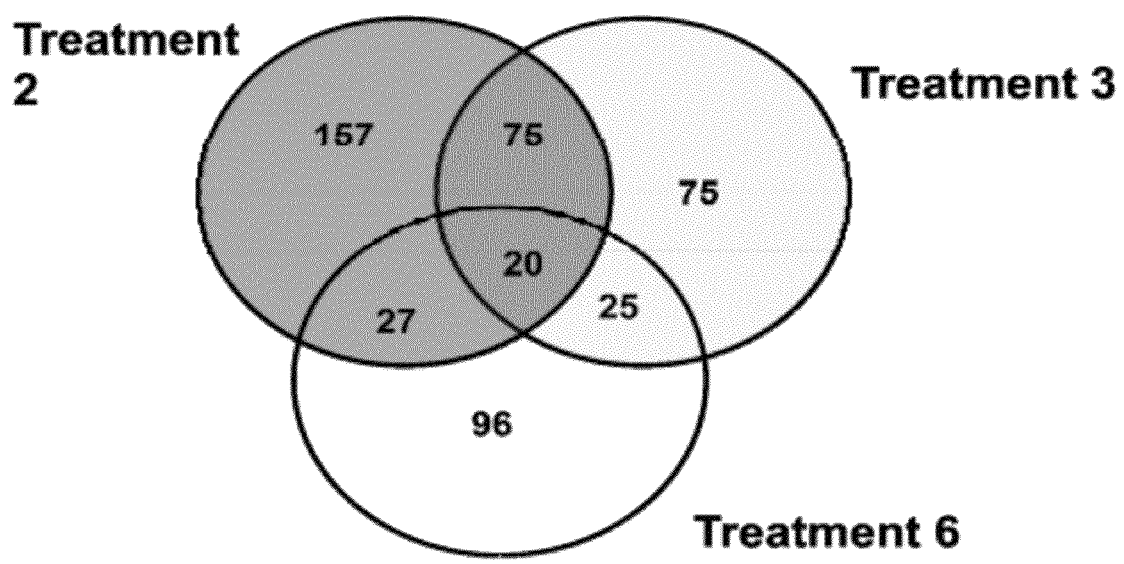
FIG. 4 shows the effects of different selenium-supplemented treatments described in Tables 3 and 4 of Example 3 on gene expression levels in chicken breast skeletal muscle relative to a basal control (no added selenium—Treatment 1).

As shown in FIG. 4, there are a number of rather surprising findings regarding the effects of different selenium-supplemented treatments on gene expression levels in the chicken breast skeletal muscle relative to control (Treatment 1: no added selenium). In particular, dietary addition of 0.3 ppm of sodium selenite (Treatment 2), SELPLEX (Treatment 3), and the pH 4.0 dependent fraction of SGP (Treatment 6) influenced breast gene expression levels whereby 279, 195 and 168 transcripts were significantly altered when compared to Treatment 1 (P<0.05, FC>1.2), respectively. 20 genes were commonly identified as being differentially expressed by all three treatments, whereas 45 genes were differentially expressed between Treatments 3 and 6. FIG. 4 also shows that there are a number of genes uniquely regulated by the different selenium-supplemented treatments.

Figure 5:
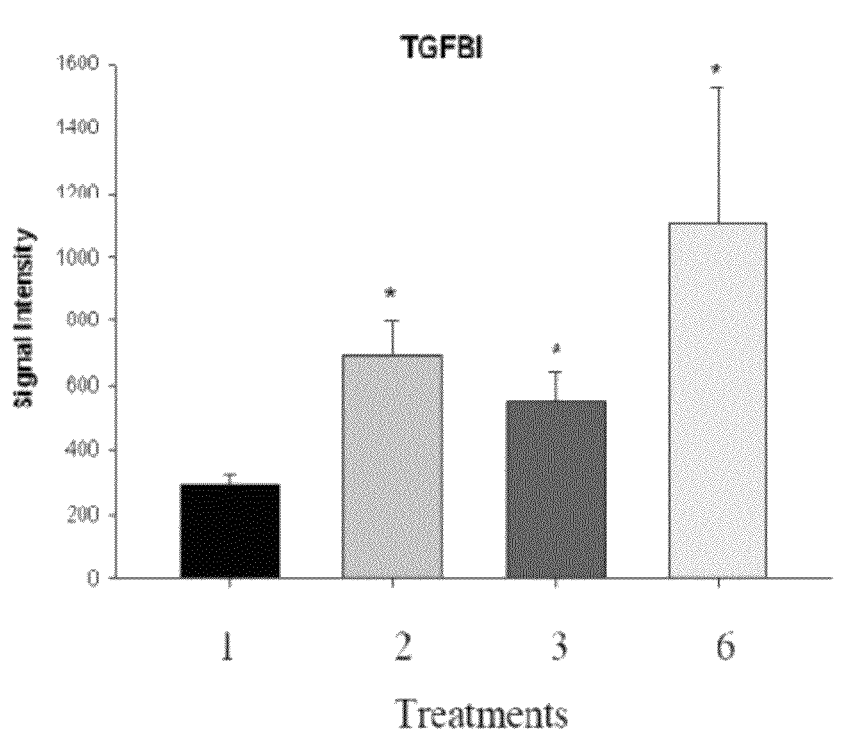
FIG. 5 shows examples of genes commonly regulated by different selenium-supplemented treatments (Treatment 2: 0.3 ppm of sodium selenite; Treatment 3: 0.3 ppm of SEL-PLEX; and Treatment 6: 0.3 ppm of pH 4.0 dependent fraction of selenoglycoprotein, relative to Treatment 1: no added selenium).
Figure 5:
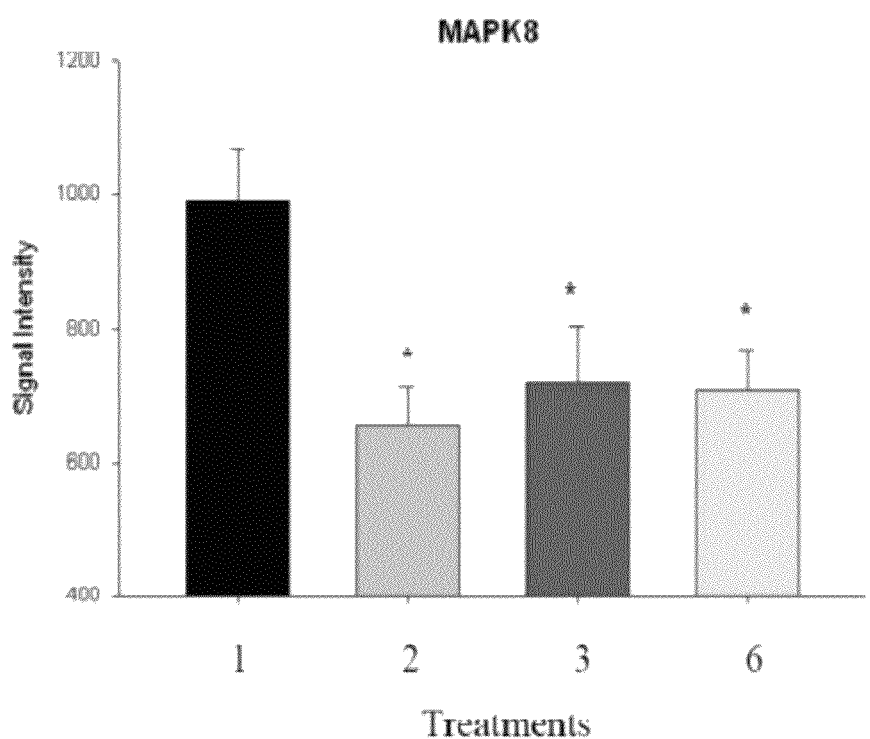

FIG. 5 provides examples of genes commonly regulated by Treatment 2 (0.3 ppm of sodium selenite); Treatment 3 (0.3 ppm of SEL-PLEX) and Treatment 6 (0.3 ppm of pH 4.0 dependent fraction of selenoglycoprotein) relative to Treatment 1 (no added selenium). The asterisk (*) indicates a P value<0.05. Transforming growth factor, beta-induced (TGFBI), 68 kDa) is one of the most consistently up-regulated genes by all treatments observed. This protein is thought to be involved in cell-matrix interactions, cell adhesion, migration and differentiation. Mutations of this gene have been linked to several forms of corneal dystrophies. Mitogen-activated protein kinase 8, (MAPK8, also known as JNK1) is a member of the MAP kinase family. MAP kinases act as an integration point for multiple biochemical signals, and are involved in a wide variety of cellular processes such as proliferation, differentiation, transcription regulation and development. MAPK8 also plays an important role in cellular oxidative stress response, immune response, as well as carbohydrate and protein metabolism through insulin signaling pathway. It is known that over activation of MAPK8 may induce insulin resistance through phosphorylation of Insulin receptor substrate 1 (IRS1).

Figure 6:
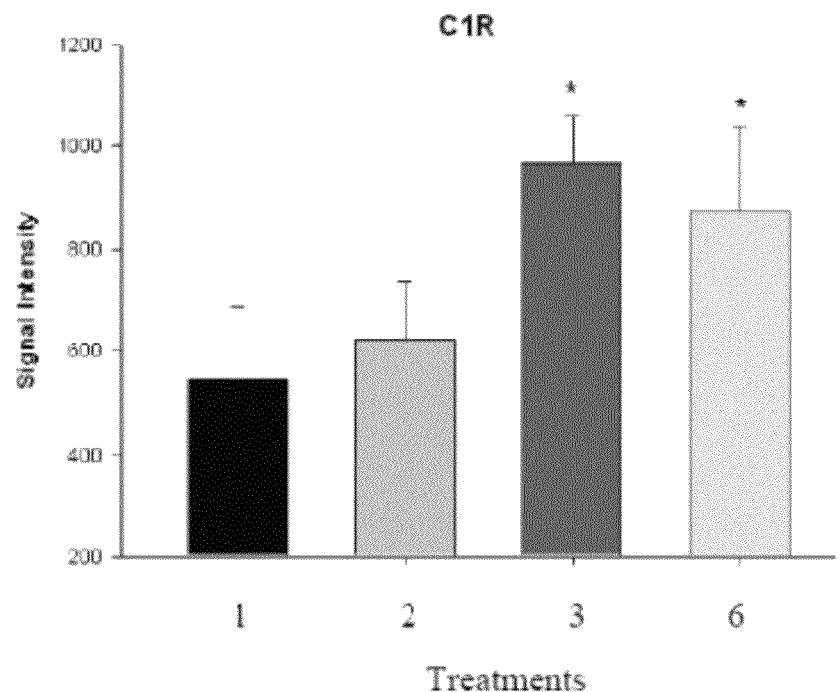
FIG. 6 shows examples of genes commonly regulated by Treatment 3 (0.3 ppm of SEL-PLEX) and Treatment 6 (0.3 ppm of pH 4.0 dependent fraction of selenoglycoprotein) relative to Treatment 1: no added selenium.
Figure 6:
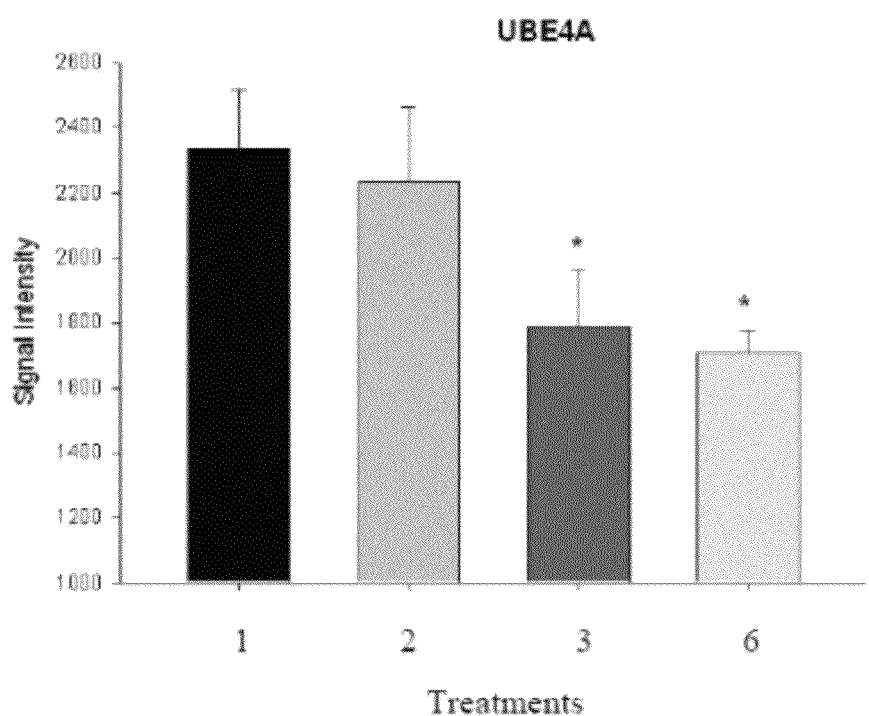

FIG. 6 provides examples of genes commonly regulated by Treatment 3 (0.3 ppm of SEL-PLEX) and Treatment 6 (0.3 ppm of pH 4.0 dependent fraction of selenoglycoprotein) relative to Treatment 1 (no added selenium). The asterisk (*) indicates a P value<0.05. Complement component 1R (C1R) is a protein involved in the complement cascade of the innate immune system and pathogen removal. As shown in FIG. 6, C1R expression levels were higher after administration of Treatment 3 as well as Treatment 6 compared to control. Also shown in FIG. 6 is the effect of administration of different treatments on ubiquitination factor E4A (UBE4A): The modification of proteins with ubiquitin is an important cellular mechanism for targeting abnormal or short-lived proteins for degradation. UBE4A encodes a U-box-type ubiquitin ligase described as an E4 ubiquitination factor. UBE4A is thought to have roles in different biochemical processes other than ubiquitination, including growth or differentiation.

Figure 7:
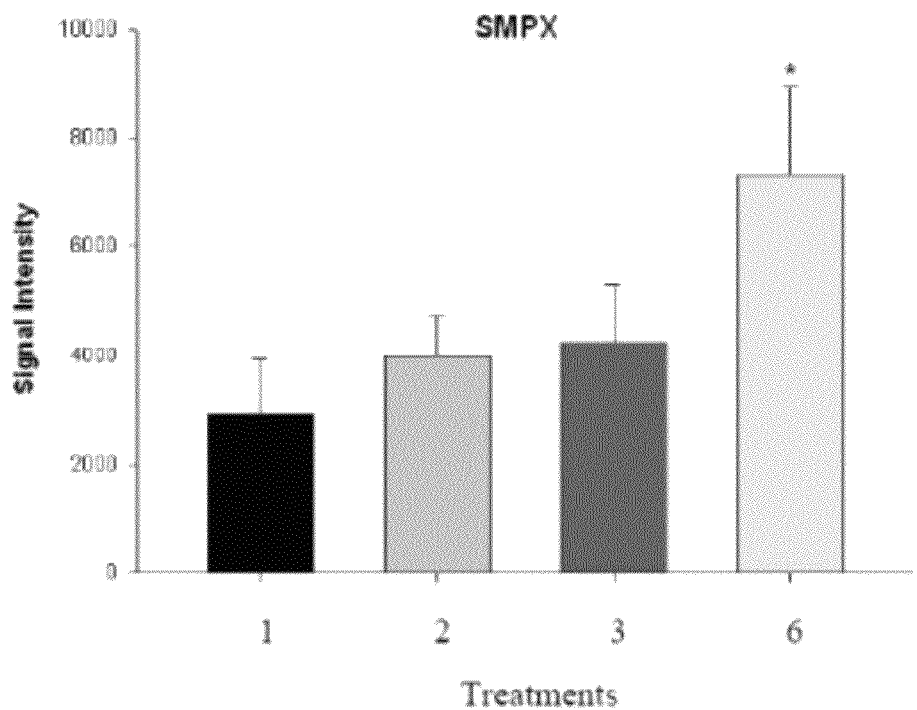
FIG. 7 shows examples of genes uniquely regulated by Treatment 6 (0.3 ppm of pH 4.0 dependent fraction of selenoglycoprotein) relative to Treatment 1 (no added selenium); Treatment 2 (0.3 ppm of sodium selenite); and Treatment 3 (0.3 ppm of SEL-PLEX).
Figure 7:
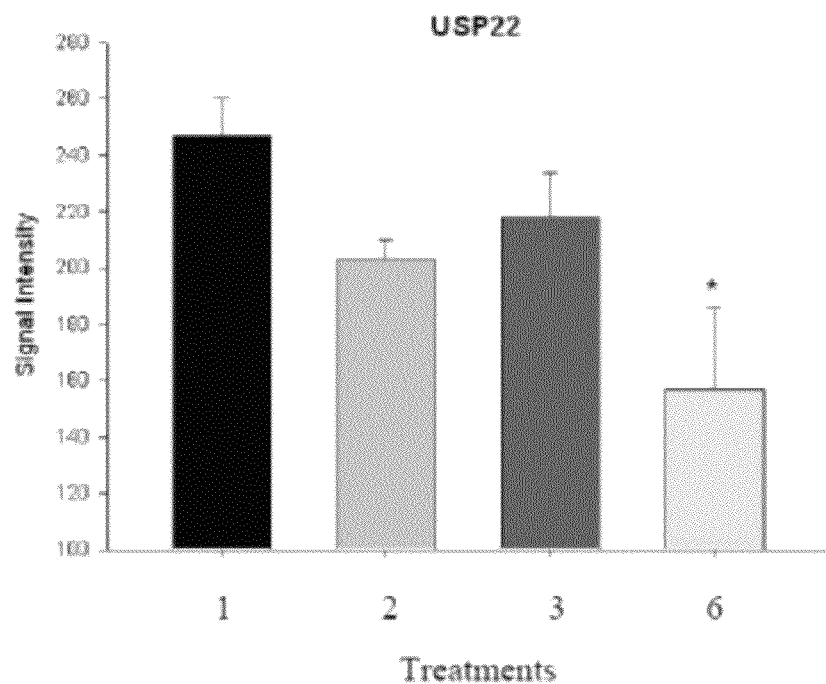
Figure 7:
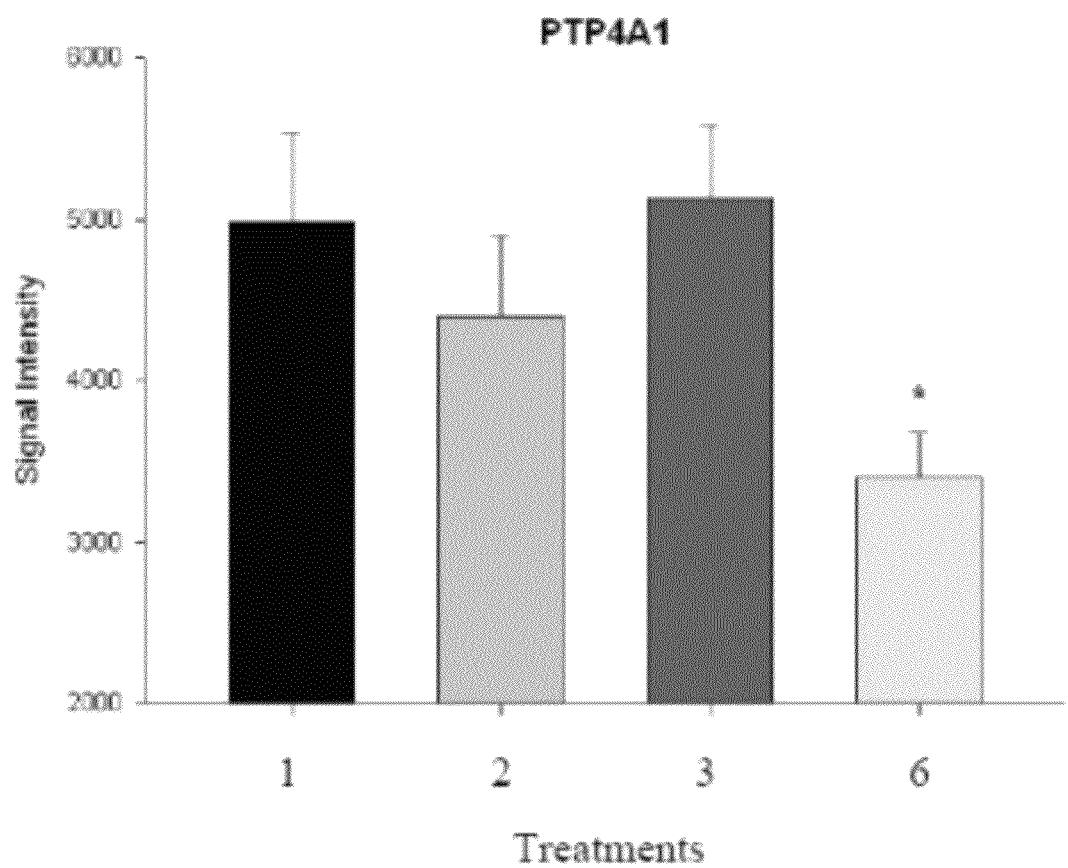

FIG. 7 provides examples of genes uniquely regulated by Treatment 6 (0.3 ppm of pH 4.0 dependent fraction of selenoglycoprotein) relative to Treatment 1 (no added selenium); Treatment 2 (0.3 ppm of sodium selenite); and Treatment 3 (0.3 ppm of SEL-PLEX). The asterisk (*) indicates a P value <0.05. Small muscle protein, X-linked (SMPX) is a small protein specifically expressed in striated muscle and plays an important role in muscle contraction. This gene was specifically up-regulated by Treatment 6. Ubiquitin specific peptidase 22 (USP22) is a gene involved in ubiquitin-dependent protein catabolic processes. USP22 has been shown to be a positive-regulator of tumor growth. Increased expression of USP22 is linked to cancer progression. Therefore, the ability to reduce or knockdown expression of USP22 may provide inhibition of tumor growth and/or cancer progression. For example, reducing the expression of USP22 can down-regulate the expression of Mdm2 and cyclin E, resulting in the up-regulated expression of p53 and p21, leading to cell cycling arrest and inhibition of human bladder tumor cell proliferation.

Protein tyrosine phosphatase type IVA, member 1 (PTP4A1) belongs to a class of prenylated protein tyrosine phosphatases (PTPs), which are cell signaling molecules that play regulatory roles in a variety of cellular processes. Over expression of this gene in mammalian cells conferred a transformed phenotype, which implicated its role in tumorigenesis. A recent study suggested that over expression of PTP4A1 is linked to the invasion and metastasis potential of lung cancer cells. As shown in FIG. 7, administration of Treatment 6 reduced the expression of PTP4A1 compared to control, whereas administration of the other treatments did not provide the same result.

A total of 642 genes were transcriptionally altered by the addition of various selenium sources to the diet, relative to basal conditions. The pH 4.0 dependent fraction of selenoglycoprotein (SGP) used in Treatment 6 affected several of the same genes that are transcriptionally altered by SEL-PLEX (Treatment 6 having been derived from SEL-PLEX). However, a more surprising result was that 75 and 96 genes were uniquely affected by Treatments 3 and 6, respectively. Thus, in some embodiments, the invention provides that while selenium as a trace element alters the expression of several notable genes, key differences in in vitro effects exist depending on the source of selenium used.

EXAMPLE 5

SelenoGlycoProteins (SGP) Encapsulation into Polymerosomes

A 1:1 mixture of SGP's that were precipitated at pH 4.0 and pH 6.0 (See Examples 1 and 2) were used in an encapsulation experiment. The Se concentration in the mixture was 3054 ppm and it contained 79.96 weight % of protein. 2 mg of SGP was suspended in 2 ml aqueous buffers of pH 5.1, 6.2 and 7.4 and the suspension was mixed overnight on a shaker. The not dissolved SGP was removed by centrifugation. To make polymerosomes, a thin film PEO-B-PCL copolymer (polymer weight: 1-2 mg per film) was deposited at the bottom of the glass vial, by solvent evaporation under vacuum. The SGP solution was added to the vials that contained copolymer film (2 ml clear SGP solution at ~1 mg/ml) and the mixture was sonicated using bath sonicator. It was vortexed for 1 min immediately after sonication to form nanosized polymerosomes. These polymerosomes were extruded using a LIPOFAST hand-held extruder to yield a narrow size distribution of average size 100 nm. The residue SGP was removed by dialysis against iso-osmolar aqueous phosphate buffer of pH 7.4. The samples were freeze-dried and analyzed for Se concentration. The atomic absorption spectroscopy (using EXCALIBUR method and instrument) was applied to measure the concentration of Se in nanocapsules (See Table 6).

TABLE 6

Encapsulation results

| Encapsulation pH | Nanocapsules (mg) | Se concentration (ppm) |
|---|---|---|
| Negative control | 8.0 | 0.02 |
| 5.1 | 4.6 | 46.5 |
| 6.2 | 3.3 | 39.6 |
| 7.4 | 8.4 | 32.2 |

EXAMPLE 6

SGP Time-release from Polymerosomes

SGP was dissolved in buffers of pH 5.1 and 7.4 and undissolved SGP was separated using methods described above. SGP solution at two pH values was encapsulated in nanosized polymer vesicles (size ~100 nm) (as described in Example 5) and unencapsulated SGP was separated by extensive dialysis. SGP encapsulation efficiencies were similar to those described in Example 4. Dialyzed polymersome suspension was concentrated by membrane centrifugation (centrifuge tubes with molecular weight cutoff of 300 kD were used). The concentrated suspensions were aliquoted into appropriate iso-osmolar buffers (pH of 5.1 or 7.4) and kept at room temperature. To evaluate the % release of SGP from polymersomes, the sample was centrifuged to separate intact vesicles at each time point. To ascertain that vesicles were effectively separated from the sample to yield a vesicle-free solution, dynamic light scattering measurements were performed on separated vesicles (retentate) and free solution (filtrate) to measure particle sizes. The majority of vesicles (size range 10-100 nm) were separated from free solution using this method. UV absorbance of free solution was measured at 280 nm and % release of SGP was calculated as $(A_{sample}-A_{initial})/(A_{final}-A_{initial})$, where $A_{initial}$ is the absorbance at day 0, and $A_{final}$ is the absorbance at the end of the study when the samples were solubilized to cause complete release.

EXAMPLE 7

Preparation of SelenoGlycoProteins (SGP) Slow Release Polymers

Synthesis of polymer A. The same sample of SGP's used in Example 5 (described in Examples 1 and 2) was used in the SGP slow release polymer preparation. 150 mg of SGP were dissolved in 2 ml of methacrylic acid and 1 ml of DI water. Some heating was applied to speed up dissolution. A sample of 0.5 ml of the solution was placed in a 5 ml vial containing 10 mg of AIBN, vortexed 1 min and the air from the tube was removed under vacuum and replaced by nitrogen. The contents of the tube were polymerized by placing the tube into a laboratory oven heated to 70 deg C. for 2 hrs. The tube was broken and the polymer was cut into thin sections and dried at high vacuum.

Synthesis of polymer B. A mixture of: 0.064 ml of methacrylic acid, 0.091 ml of 2-hydroxyethyl-methacrylate, 1.427 ml ethylene glycol dimethacrylate and 10 mg AIBN were placed in a 5 ml vial and stirred with magnetic stirring bar, followed by 75 mg of SGP dissolved in a mixture of 1.5 ml acetic acid and 0.75 ml DI water. The air in the vial was replaced with nitrogen and the vial was sealed and placed for 4 hrs in an oil bath at 70 deg C. The vial was broken and the polymer monolith was crushed into powder in a porcelain mortar. The volatiles were removed from the polymer under high vacuum.

SGP time release. The same, SGP slow release protocol was applied to each of the polymers (A and B). 333.7±0.1 mg of polymer was placed in a 15 ml centrifuge tube containing 5ml of citrate buffer (pH 5.0) and the tube was slowly shacked for four hours. The tubes were then centrifuged and supernatant collected while the polymer pellet was washed with two 8 ml volumes of DI water and freeze-dried. ~21 mg were taken out of the freeze-dried sample for Se analysis. The SGP extractions were repeated two more times. The weights of the samples were recorded. All of the samples lost weight during these treatments (See Tables 7 and 8).

TABLE 7

Milligrams of polymer for release

| Polymer | Initial | Post 1st Wash | Post 2nd Wash | Post 3rd Wash |
|---|---|---|---|---|
| A | 333.6 | 271.4 | 235.6 | 207.8 |
| B | 333.6 | 301.6 | 281.1 | 254 |

TABLE 8

Milligrams of polymer taken for Se analysis

| Polymer | Initial | Post 1st Wash | Post 2nd Wash | Post 3rd Wash |
|---|---|---|---|---|
| A | 21.1 | 20.5 | 20.9 | 20.6 |
| B | 20.6 | 20.5 | 20.6 | 20.8 |

To estimate concentration of the released SGP, the UV absorbance at 280 nm of the supernatants were measured and compared with the SGP calibration curve prepared in the same buffer (See Table 9).

TABLE 9

| | abs | ml in 2 ml dilution | mg SGP'S/ml in original solution | mg SGP released during interval |
|---|---|---|---|---|
| Polymer A | | | | |
| 1st wash | 0.298 | 0.1 | 0.781 | 3.907 |
| 2nd wash | 0.349 | 0.5 | 0.183 | 0.913 |
| 3rd wash | 0.353 | Not diluted | 0.046 | 0.231 |
| Polymer B | | | | |
| 1st wash | 0.35 | 0.25 | 0.366 | 1.831 |
| 2nd wash | 0.572 | Not diluted | 0.074 | 0.372 |
| 3rd wash | 0.251 | Not diluted | 0.033 | 0.165 |

The atomic absorption spectroscopy (using EXCALIBUR method and instrument) was applied to measure the concentration of residue Se in the slow release polymer (See Table 10).

TABLE 10

| Sample | Polymer A Se concentration (ppm) | Polymer B Se concentration (ppm) |
|---|---|---|
| Original sample | 318.6 | 127.1 |
| After 1st wash | 268.8 | 116.1 |
| After 2nd wash | 222.3 | 108.7 |
| After 3rd wash | 215.3 | 92.3 |

According to the measurements of Se concentration in the residue pellets, 36.08% of SGP were released from Polymer A, after triple, 4 hrs washes (12 hrs total). During the same treatment 30.11% of SGP were released from Polymer B.

EXAMPLE 8

Alkaline Extraction of Intracellular Yeast Proteins 200.0 g of SEL-PLEX were taken for extraction with 1 L of 0.1M sodium hydroxide at 60° C. for 8 hours. After this time the mixture was centrifuged at 14,000×g/10 min/10° C. and the pellet was washed two times with 400 ml of DI water each. The residue pellet weighed 54.5 g (after freeze-drying). The supernatant and washes were combined and their pH was adjusted to 6.6 by the addition of concentrated hydrochloric acid. Traces of a precipitate formed during neutralization and were separated by centrifugation before the clear supernatant was concentrated using Amicon® 10 kDa ultrafiltration devices. The concentrate was washed with two 100 ml portions of DI water and freeze dried yielding 64.0 g of brown solid. Combined filtrates (total volume 2l) were analyzed for Selenium while the solid products from separation were analyzed for Selenium and Nitrogen/Protein. The results are given in the TABLE 11.

TABLE 11

| Alkaline extraction | | | | | |
|---|---|---|---|---|---|
| | Weight (g) | Se (ppm) | Protein (w %) | Se total (mg) | Se (%) of total |
| Se YCW | 200.0 | 1600 | 37.0 | 320.0 | 100.0 |
| Pellet after pH 11.5 extraction | 54.5 | 760 | 2.9 | 41.4 | 12.9 |
| Supernatant pH 6.6 MW > 10 kDa | 64.0 | 1918 | 52.9 | 122.8 | 38.3 |
| Supernatant 2 L MW < 10 kDa | NA (not analyzed) | 1909 | NA | 155.8 | 48.7 |

The mass balance and the selenium distribution indicate 40.7% loss of mass and 48.7% loss of Selenium which were not recovered by ultra-filtration through 10 kDa membrane. β-Nucleophilic/thermal eliminations of $MeSe^{-1}$ and $HSe^{-1}$ and oxidized forms of these functional groups from selenium-containing peptides, resulted in degradation of the original chemical structure of SGP's and loss of mass and selenium into the filtrate. The production process generates increased volume and heightened concentration of selenium in the filtrate which results in a waste stream that may have harmful or deleterious effects (e.g. harmful to the environment). In contrast, the methods of the present invention provide acidic extraction and pH dependent fractionation of yeast SGPs (e.g. in a large scale commercial process). Under conditions of varying temperature it was found that the traditional/conventional technique of alkaline hydrolysis would not work in order to extract selenoglycoproteins from yeast cells. As described herein, extracting SGP's from yeast cells using acidic extraction was discovered to be successful. The most surprising nature of this method is that the protein composition of various fractions obtained by chromatographic separations (e.g. ion exchange chromatography, size exclusion chromatography) of different SGP fractions from pH dependent precipitation, was the same or very similar, according to electrophoretic methods (gel electrophoresis and capillary electrophoresis) that have been applied. As described herein, extraction of selenoglycoproteins from selenium enriched yeast was successful at a low pH (e.g., 1.5). Although an understanding of a mechanism is not needed to practice the invention and the invention is not limited to any particular mechanism of action, in some embodiments, under the acidic used for conditions SGP extraction, the protein cores are not hydrolyzed significantly and survive mostly in their original form.

EXAMPLE 9

Polymersome Encapsulation of Selenoglycoprotein

Selenoglycoproteins extracted from SEL-PLEX and precipitated from the intracellular lysate at pH 4.0 were encapsulated in polymersomes. Specifically, the pH 4.0 dependent fraction of selenoglycoproteins were encapsulated in polymers comprised of poly(ethylene oxide)-block-poly($\epsilon$-caprolactone) (PEO-b-PCL) based diblock copolymers.

In order to generate selenoglycoprotein encapsulated polymersomes, the pH dependent selenoglycoprotein fractions were dissolved in an aqueous buffer of pH in the range of 3.0-5.0 at concentrations of 1-20 mg selenoglycoprotein/ml of aqueous solution. Briefly, PEO(2k)-b-PCL(12k)-based diblock copolymer was dissolved in an organic solvent (e.g. methylene chloride, tetrahydrofuran, or dimethyl sulfoxide) to yield 1 mM PEO-b-PCL polymer in organic solution. The solution was then deposited on a roughened TEFLON strip (approximately 1"×1"×1/16" thick) and the strip placed on the bottom of a glass vial with roughened side facing up. The solvent was evaporated under vacuum at ambient temperature for 24-48 hrs to obtain dried film of copolymer weighing 1-10 mg.

Figure 9:
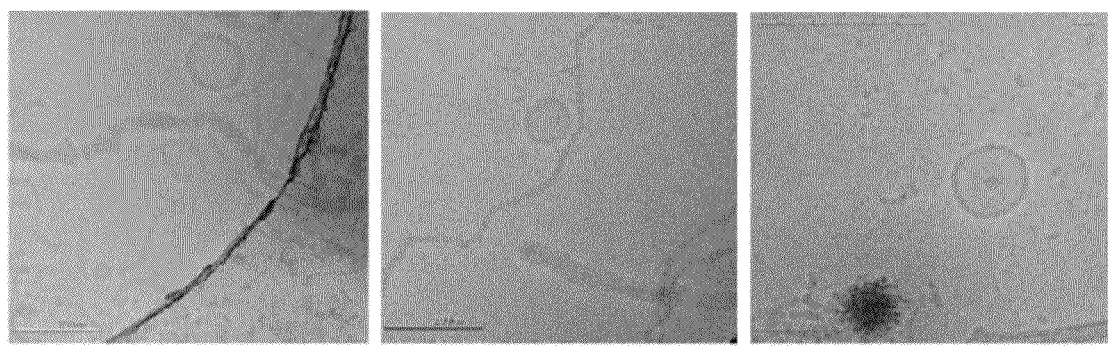
FIG. 9 shows Cryogenic Tunneling Electron Microscopy (cryo-TEM) images of polymersome encapsulated selenoglycoprotein at pH 7.4.

These films were then hydrated with 2-3 ml of pH 4.0 dependent selenoglycoprotein fraction-containing aqueous solution and the mixture sonicated in a bath sonicator at 20-100 Hz for 1-2 hrs. After the sonication was complete, vials were immediately vortexed for 1-2 min to form polymersomes that encapsulate the selenoglycoproteins in the aqueous core of PEO-b-PCL-based polymer vesicles. The polymersomes were then rapidly extruded through a polycarbonate membrane of desired pore size using a LIPOSOFAST extruder to obtain a desired average diameter of the polymersomes, in this case, ranging from 50-300 nm. Extruded polymersomes were then injected into a dialysis cassette for solution exchange against an iso-osmatic buffer of pH in the range of 5-7.4 for 24 hours to remove all un-encapsulated selenoglycoprotin. As further described below, FIG. 9 shows cryo-TEM images of polymersome encapsulated selenoglycoproteins at pH 7.4.

The polymersome encapsulated selenoglycoproteins were further characterized The results of selenium content analysis in various batches of polymersomes are shown in Table 12. As indicated, the batches varied by the amount of selenoglycoprotein (mg/ml) used for the encapsulation reaction as well as the pH. One ml of polymersome encapsulated selenoglycoproteins samples were freeze-dried and the white powders weighed and inspected under 200× magnification. Whole amounts of polymersome encapsulated selenoglycoproteins were dissolved using concentrated acids: perchloric, nitric and hydrochloric acids at a temperature between 100° C. to 175° C., and the solutions diluted to 50 ml with deionized (DI) water. The solutions were then analyzed using a Millenium Excalibur instrument and methodology.

TABLE 12

| | Selenium content within polymersome encapsulated selenoglycoproteins | | | |
|---|---|---|---|---|
| Sp# | Starting concentration of selenoglycoprotein [mg/ml] | pH | Freeze-dried powder weight [mg] | Se [ppm] |
| 1 | 2.5 | 7.4 | 8.9 | 274 |
| 2 | 5.0 | 7.4 | 13.6 | 835 |
| 3 | 10.0 | 7.4 | 10.3 | 493 |
| 4 | 2.5 | 5.0 | 37.8 | 125 |
| 5 | 5.0 | 5.0 | 25.0 | 168 |
| 6 | 10.0 | 5.0 | 10.8 | 999 |

Figure 8:
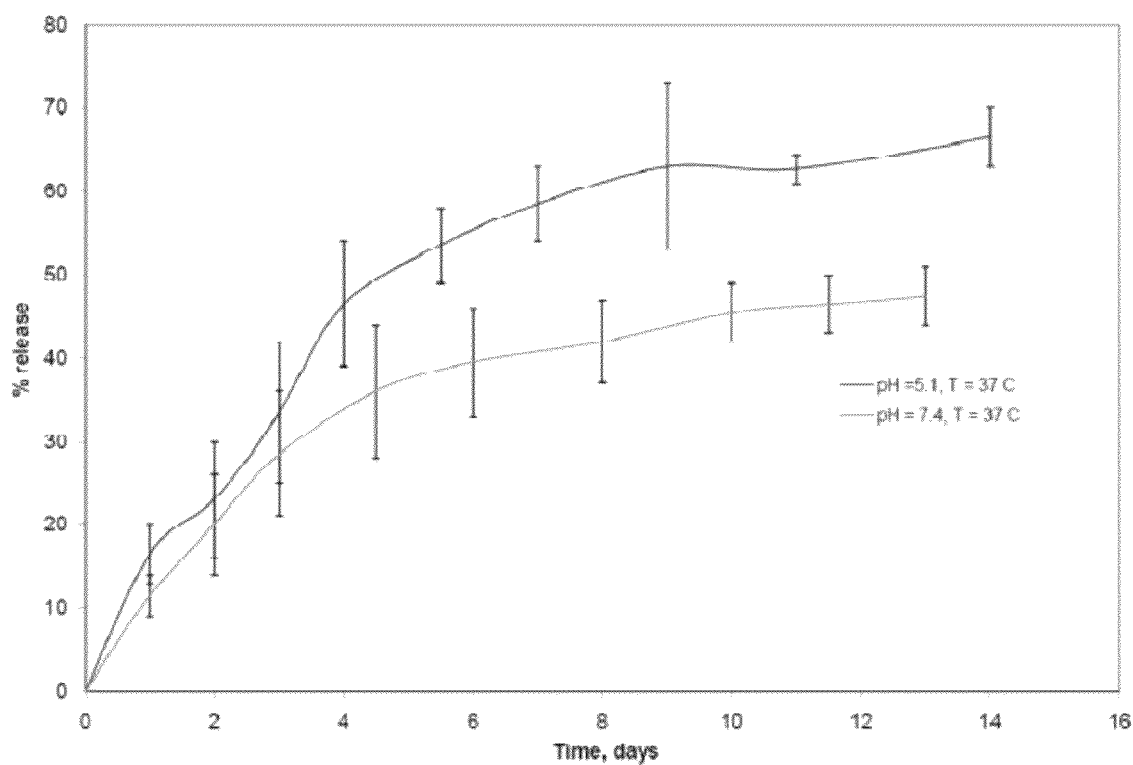
FIG. 8 shows the cumulative in vitro release of selenoglycoproteins from polymersome encapsulated selenoglycoprotein at two pH values and 37° C. in one embodiment of the invention.

Release of Selenoglycoproteins from Selected Formulations:

Release of selenoglycoprotein (SGP) from polymersome batch formulations #3 and 6 from Table 12 above, prepared with 10 mg/ml of SGP suspension and dialyzed against buffers of pH 7.4 and 5.1 respectively, was monitored over a 14-day period at 37° C. To monitor release of selenoglycoproteins from the polymersome encapsulated selenoglycoprotein, dialyzed suspensions were concentrated by membrane centrifugation (centrifuge tubes with molecular weight cutoff of 300 kD were used). The concentrated suspensions were aliquoted into iso-osmolar buffers (pH of 5.1 or 7.4) and kept at room temperature with N=2 samples for each time point. To evaluate the % release of selenoglycoprotein from the polymersomes, the samples were centrifuged to separate intact polymersomes at each time point. To ascertain that polymersomes were effectively separated from the selenoglycoprotein sample, dynamic light scattering measurements were performed on separated vesicles (retentate) and free solution (filtrate) to measure particle sizes. UV absorbance of free solution were measured at 280 nm and % release of selenoglycoproteins was calculated as $(A_{sample}-A_{initial})/(A_{final}-A_{initial})$, where $A_{initial}$ is the absorbance at day 0, and $A_{final}$ is the absorbance at the end of the study when the samples were solubilized to cause complete release. FIG. 8 shows the results of these studies. Steady-state release of up to 70% of encapsulated selenoglycoprotein was observed at pH 5.1 whereas up to 50% of selenoglycoprotein was released from the polymersome core at pH 7.4 over the 14-day period. The faster initial release rate at lower pH is thought to occur due to acid-catalyzed hydrolysis of polymersome membrane, followed by steady diffusion of selenoglycoprotein across polymersome membrane. These release profiles are remarkably similar to those of doxorubicin, a cancer therapeutic, encapsulated inside PEO-b-PCL-based polymersomes (See, e.g., Ghoroghchian et al. Macromolecules, 2006, 39 (5), 1673-1675). These data confirm show encapsulation of selenoglycoproteins even at a relatively high loading concentration does not affect the release pattern in a negative way.

CryoTEM Imaging of Polymersome Encapsulated Selenoglyocprotein:

An sample of polymersome encapsulated selenoglyocprotein was prepared with a starting selenoglycoprotein concentration of 10 mg/ml and dialyzed against iso-osmolar PBS buffer. This sample was imaged by cryo-TEM at magnifications of 21,000× and 52,000× to obtain visual identification of successful selenoglycoprotein encapsulation inside polymersomes. Cryo-TEM allows for the imaging of specimens at cryogenic temperatures in their native hydrated states thereby preventing any undesirable conformational changes. Representative sample images are shown in FIG. 9. Generally, uniform spherical polymersomes of sizes around 100 nm or slightly smaller were observed in the imaged sample. In some cases, approximately spherical aggregates of amorphous material were observed in addition to polymersomes. These aggregates may be comprised of selenoglyocprotein released from the polymersome core and which further precipitates due to the difference in pH from the inside to the outside of the polymersome by the time the samples are imaged.

REFERENCES

The following references are herein incorporated by reference in their entireties, as if fully set forth herein.
1. Demirci A., Pometto III A. L. 'Enhanced Organically Bound Selenium Yeast Production By Fed-Batch Fermentation' J. Agric. Food Chem. 47, 2496-2500 (1999).
2. Demirci A., Pometto III A. L. 'Production of Organically Bound Selenium Yeast by Continuous Fermentation' J. Agric. Food Chem. 47, 2491-2495 (1999).
3. Ouerdane L., Mester Z. 'Production and Characterization of Fully Selenomethionine-Labelled *Saccharomyces cerevisiae*' J. Agric. Food Chem. 56,11792-11799, (2008).
4. Korhola. M.; Vainio, A.; Edaelman, K. 'Selenium yeast' Ann. Clin. Res. 18, 65-68, (1986).
5. Surai P. F. Natural Antoxidants in Avian Nutrition and Reproduction' Nottingham University Press 2002, 234-236 (2002).
6. Kelly, M. P.; Power R. F. 'Fractionation and identification of the major selenium compounds in selenized yeast' J. Dairy Sci. 78, 237-242 (1995).
7. McSheehy, S.; Kelly, J.; Tessier, L.; Mester, Z. 'Identification of Selenomethionine in selenized yeast using two-dimensional liquid chromatography-mass spectrometry based proteomic analysis' Analyst 130, 35-37 (2005).
8. Sedmak J. J. 'Production of beta-Glucans and Mannans' US Patent Appl. Publication Pub. No.: US 2006/0263415 A1.
9. Rayman, M. P. 'The importance of selenium to human health' The Lancet 356, 233-241 (2000).
10. McKenzie, R. C.; Rafferty, T. S.; Beckett, G. J. 'Selenium: an essential element for immune function' Trends in Immunology 19, 342-345 (1998).
11. Tapiero, H.; Townsend, D. M.; Tew, K. D. 'The antioxidant role of selenium and selenocompounds' Biomedicine&Pharmacotherapy' 57, 134-144 (2003).
12. Combs, G. F.; Grey, W. P. 'Chemopreventive Agents: Selenium' Pharmacol. Ther. 79, 179-192 (1998).
13. Clark, L. C.; Combs Jr., G. F.; Turnbull, B. W. et al. 'Effects of Selenium Supplementation for Cancer Prevention in Patients with Carcinoma of Skin' J. Am. Med. Assoc. 276, 1957-1963 (1996).
14. Otero, M. A.; Vasallo, M. C.; Verdecia, O.; Fernandez, V.; Betancourt, D. 'A Process for the Complete Fractionation of Baker's Yeast' J. Chem. Tech. Biotechnol. 66, 67-71 (1996).
15. Roberge, M. T.; Borgerding, A. J.; Finley, J. W. 'Speciation of Selenium Compounds from High Selenium Broccoli Is Affected by the Extracting Solution' J. Agric. Food Chem. 51, 4191-4197 (2003).
16. Furnsinn et al., Int. J of Obesity and Related Metab. Dis., 19, 458-463 (1995).
17. El-Bayoumy, The role of selenium in cancer prevention, Philadelphia, Lippincott, 1-15, 1991.
18. Yu et al. Biol Trace Elem Res, 56: 117-124 (1997).
19. Yoshizawa et al., J Natl Cancer Inst, 90: 1219-1224, (1998).
20. Brooks, et al., J Urol, 166: 2034-2038, (2001).
21. Garland et al., J. Am. Coll Nutr., 12: 400-11 (1993); Ghadirian et al., Cancer Detect Prey, 24: 305-13 (2000).
22. Martin, Remington's Pharmaceutical Sciences, 15th Ed., Mack Publ. Co., Easton, Pa. (1975).
23. Goehring et al., J. Anim. Sci. 59, 725-732 (1984); Gerloff et al., J. Anim. Sci. 70, 3934-3940 (1992).
24. Meister and Anderson, Annu Rev. Biochem. 52, 711-760 (1983).
25. Deleve and Kaplowitz, Pharm. Ther. 52, 287-305 (1991).
26. Palmer and Paulson, Nutr. Rev. 55, 353-361 (1997).
27. Salonen et al., Am. J. Epidemiol. 120: 342-349 (1984).
28. Willett et al., Lancet 2: 130-134 (1983).
29. Virtamo et al., Cancer 60: 145-148 (1987).
30. Ip, J. Nutr. 128: 1845-1854 (1998).
31. Ip and Daniel, Cancer Res. 45: 61-65 (1985).
32. Pence et al., 102: 759-761 (1994).
33. Bedwal, R. S., et al., Medical Hypotheses, 41 (2):150-159 (August 1993).
34. Ferris G. M. Lloyd, et al., App. Clin. Biochem., 26:83-88 (1989).
35. Furnsinn, C. et al., Internat'l J. of Obesity and Related Metab. Dis., 19(7):458-463 (1995).
36. Mahan, Proceedings of the 15th Annual Symposium Nottingham University Press, Nottingham, UK, pp. 523-535 (1999).
37. Discher et al. Journal of Physical Chemistry B (2002), 106(11), 2848-2854.
38. Couvreur et al. Crit Rev Ther Drug Carrier Syst. 2002; 19(2):99-134.
39. Mosbach. Trends in Biochemical Sciences, Vol. 7, pp. 92-96, 1994.
40. Wulff. Trends in Biotechnology, Vol. 11, pp. 85-87, 1993.
41. Andersson, et al., Molecular Interactions in Bioseparations (Ngo. T. T. ed.), pp. 383-394.

What is claimed is:
1. A method for preparation of soluble selenoglycoproteins comprising:
   a) providing selenium enriched yeast;
   b) exposing the selenium enriched yeast to acidic conditions followed by centrifugation to generate
      i) a pellet comprising acid insoluble material; and
      ii) a liquid phase comprising the extract of selenium enriched yeast soluble under the acidic conditions;
   c) precipitating selenoglycoproteins from the liquid phase comprising the extract of selenium enriched yeast soluble under the acidic conditions via raising the pH of the liquid phase; and
   d) separating the precipitated selenoglycoproteins from the liquid phase.
2. The method of claim 1, wherein the acidic conditions are obtained using acidic buffer or the addition of an acid.
3. The method of claim 2, wherein the acid is hydrochloric acid.
4. The method of claim 1, wherein exposing the selenium enriched yeast to acidic conditions comprises exposing the selenium enriched yeast to a pH between 1.5 and pH 6.5.
5. The method of claim 4, wherein the pH is 1.5.
6. The method of claim 1, wherein the selenium enriched yeast are exposed to acidic conditions for between one and twenty-four hours.

7. The method of claim 1, wherein the selenium enriched yeast are exposed to acidic conditions for between five and ten hours.

8. The method of claim 1, wherein the selenium enriched yeast are exposed to acidic conditions for about 8 hours.

9. The method of claim 1, wherein exposing the selenium enriched yeast to acidic conditions occurs at a temperature greater than room temperature.

10. The method of claim 9, wherein the temperature is between 50° C. and 100° C.

11. The method of claim 9, wherein the temperature is between 70° C. and 85° C.

12. The method of claim 9, wherein the temperature is 80° C.

13. The method of claim 1, wherein selenoglycoproteins are precipitated from the liquid phase at a variety of pH conditions to generate multiple pH dependent fractions of soluble selenoglycoproteins.

14. The method of claim 13, wherein the multiple pH dependent fractions of soluble selenoglycoproteins are generated at pH values of 1.85, 3.0, 4.0 and 6.0.

15. The method of claim 1, wherein separating the precipitated selenoglycoproteins from the liquid phase comprises centrifugation to form a pellet of the precipitated selenoglycoproteins followed by removal of the liquid phase from the precipitated selenoglycoproteins.

16. The method of claim 1, wherein the method is used to create a fraction of soluble selenoglycoproteins precipitated at a value selected from the group consisting of pH of 1.85, 3.0, 4.0 and 6.0.

17. The method of claim 1, wherein the selenium enriched yeast are dried, nonviable selenium-enriched yeast containing 2% or less inorganic selenium.

* * * * *